(12) United States Patent
Jardine et al.

(10) Patent No.: US 9,908,854 B2
(45) Date of Patent: Mar. 6, 2018

(54) PROCESS FOR SYNTHESIZING ERGOTHIONEINE AND RELATED COMPOUNDS

(71) Applicant: University of Cape Town, Cape Town (ZA)

(72) Inventors: Moegamat Anwar Jardine, Cape Town (ZA); Lutete Peguy Khonde, Cape Town (ZA)

(73) Assignee: University of Cape Town, Cape Town (ZA)

( * ) Notice: Subject to any disclaimer, the term of this patent is extended or adjusted under 35 U.S.C. 154(b) by 0 days.

(21) Appl. No.: 15/513,237

(22) PCT Filed: Sep. 22, 2015

(86) PCT No.: PCT/IB2015/001668
§ 371 (c)(1),
(2) Date: Mar. 22, 2017

(87) PCT Pub. No.: WO2016/046618
PCT Pub. Date: Mar. 31, 2016

(65) Prior Publication Data
US 2017/0305865 A1    Oct. 26, 2017

(30) Foreign Application Priority Data
Sep. 22, 2014  (GB) .................................. 1416678.9

(51) Int. Cl.
*C07D 233/84*    (2006.01)
*A61K 31/4164*    (2006.01)

(52) U.S. Cl.
CPC ........ *C07D 233/84* (2013.01); *A61K 31/4164* (2013.01)

(58) Field of Classification Search
CPC .................................................... C07D 233/84
See application file for complete search history.

(56) References Cited

U.S. PATENT DOCUMENTS

2012/0136159 A1    5/2012 Erdelmeier

FOREIGN PATENT DOCUMENTS

WO         2014100752 A1    6/2014

OTHER PUBLICATIONS

Erdelmeier, et al., "Cysteine as a sustainable sulfur reagent for the protecting-group-free systhesis of sulfur-containing amino acids: biomimetic synthesis of L-ergothioneine in water", Gren Chem, 2012, 14, 2256-1165.

International Search Report for PCT/IB2015/001668 dated Sep. 22, 2015.
Written Opinion for PCT/IB2015/001668 dated Sep. 22, 2015.

*Primary Examiner* — Shawquia Jackson
(74) *Attorney, Agent, or Firm* — Andrus Intellectual Property Law, LLP

(57) ABSTRACT

The invention provides a process for synthesising a compound of formula V

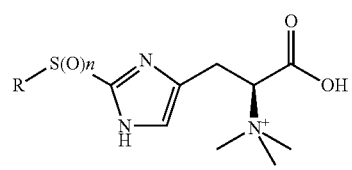

wherein:
n is 0, 1 or 2; and
R is H or

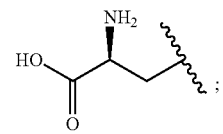

or a physiologically acceptable salt, tautomer, stereoisomer or mixture of stereoisomers thereof. The process utilizes a N-benzyl protected histidine rather than the unprotected form of histidine. The process of the invention comprises the steps of: (a) deprotecting a N-benzyl protected histidine of formula 11 to form N-benzyl histidine of formula 12; (b) converting compound 12 to (S)-3-(1-benzyl-1H-imidazol-4-yl)-2-(dimethylamino)propanoic acid of formula 13; (c) converting compound 13 to (2S)-N,N,N-2-trimethylethanaminium-3-(1-benzyl-1H-imidazol-4-yl)propanoic acid of formula 14; (d) brominating the imidazole ring of the compound of formula 14 to form 5-bromohercynine lactone (reactive intermediate); and (e) converting the 5-bromohercynine lactone of step (d) to (β-amino-β-carboxyethyl) ergothioneine sulfide of formula 15. The process optionally further includes one of steps (f) to (h): (f) converting the compound of formula 15 to a sulfoxide; (g) converting the compound of formula 15 to a sulfone; or (h) converting the compound of formula 15 to ergothioneine (ESH).

20 Claims, 24 Drawing Sheets

PROCESS FOR SYNTHESIZING ERGOTHIONEINE AND RELATED COMPOUNDS

CROSS-REFERENCE TO RELATED APPLICATIONS

The present application is U.S. national stage of International Application PCT/IB2015/001668, filed on Sep. 22, 2015, which international application was published on Mar. 31, 2016, as International Publication No. WO 2016/046618. The International Application claims priority to British Patent Application No. GB 1416678.9, filed on Sep. 22, 2014, the contents of which applications are incorporated herein by reference in their entireties.

FIELD OF THE INVENTION

A process is described for synthesising ergothioneine and related compounds of formula V.

BACKGROUND TO THE INVENTION

Many gram positive bacteria, such as *Mycobacterium tuberculosis* produce ergothioneine (ESH) as protective small molecule thiol.[1,2,3] ESH is a thiohistidine betaine derivative with a thiol group at the C2 atom (ε-position) of the imidazole ring (Scheme 1). Recently, it was found that ESH is actively secreted into culture media by *Mycobacterium smegmatis*[4] and present knowledge indicates that ESH may play a critical role in the in vivo and in vitro survival of *mycobacteria*.

A structural variant of ESH, ovothiol A, also serves as an anti-oxidant albeit in sea urchin eggs as well as in the pathogens, *Leishmania major* and *Trypanosoma cruzi*.[5]

Humans do not synthesize ESH, but possess an active transport system, a cation transporter (OCTN1) with high specificity for its uptake from dietary sources.[6,7]

In 1956, Heath et al elucidated ESH biosynthesis in *Claviceps purpurea*. He demonstrated that histidine or a compound closely related to histidine might be a precursor of ESH, and subsequent publications disclosed the biosynthetic assembly of ESH utilizing organisms such as *Neurospora crassa* and *Mycobacterium smegmatis* with the aid of radio isotopic labelling ($^{14}$C and $^{35}$S).[8,9,10]

Melville et al further established the participation of the S-(β-amino-β-carboxyethyl)ergothioneine sulfoxide as an intermediate in ESH synthesis by incubation of hercynine in cell-free extracts of *Neurospora crassa* in the presence of $O_2$ and $Fe^{2+}$.[11]

The sulfoxide is the substrate for the mycobacterial enzyme, EgtE. However, the absolute chirality of the sulfoxide is not known for the natural substrate or the synthetic one. Prior synthesis of intermediate (II) was reported in 1974 but was elaborate and irreproducible, and resulted in a low overall yield of 8.5%.[15] The authors reported only the position of the aromatic proton resonance and no further structural confirmation. An optical rotation, $[\alpha]_D$ +74.4 (c=0.5, $H_2O$), was reported and could not be reconciled with the authentic natural product $[\alpha]_D$ +9.1 (c=0.5, $H_2O$). However, the m.p. of both natural and synthetic product was recorded as 188-190° C. None-the-less, it was claimed that synthetic S-(β-amino-β-carboxyethyl)ergothioneine sulfoxide (II) was extensively cleaved to ESH by crude cell free extracts of *Neurospora Crassa*.

It has now been established that ESH is synthesized by the sequential action of five enzymes, encoded by the genes egtA, egtB, egtC, egtD and egtE (Scheme 1).[12] EgtA is considered to be a γ-glutamyl cysteine ligase and catalyzes the formation of γ-glutamylcysteine. Histidine is methylated by an S-adenosylmethionine (SAM) dependant methyl transferase, EgtD, to give the trimethyl ammonium betaine, hercynine. Hercynine is then converted into S-(β-amino-β-carboxyethyl)ergothioneine sulfoxide (II), via an iron (II)-dependent oxidase (EgtB) which requires oxygen and γ-glutamylcysteine to produce γ-glutamylcysteinylhercynine (I). The exact nature of the latter transformation, in particular the sulfoxide formation, is still under investigation. Subsequently, a putative class-II glutamine amidotransamidase, EgtC, mediates the hydrolysis of the N-terminus glutamic acid, providing S-(β-amino-β-carboxyethyl)ergothioneine sulfoxide (II). Finally, EgtE, a pyridoxal 5-phosphate (PLP)-dependent β-lyase gives the final product, ESH.

Recently, the research focus with regard to these mercapohistidines has shed light on the mechanism of C—S bond formation at the δ- or ε-positions of the imidazole ring.[13] OvoA is an iron (II) dependent sulfoxide synthase which catalyzes the first step in ovothiol A synthesis and is a homolog of EgtB. Interestingly, the substrate specificity of EgtB vs. OvoA in achieving C—S bond formation differs significantly. OvoA is very selective for its sulfur donor substrate and only accept L-cysteine while it prefers histidine as co-substrate. However, EgtB require γ-glutamyl-L-cysteine as sulfur donor. Furthermore, it is selective toward α-N,N,N-methylation on the histidine, i.e. hercynine as co-substrate. Surprisingly, OvoA switches its sulfurization pattern on the histidine ring from the δ-carbon to the ε-carbon depending on the level of α-N-methylation.[14] Thus, OvoA converts hercynine directly into S-(β-amino-β-carboxyethyl)ergothioneine sulfoxide (II) and produces a minor amount of the δ-sulfoxide (ovothiol substitution pattern) when α-N,N-dimethyl histidine is used as the co-substrate (Scheme 1).

Scheme 1: ESH biosynthesis

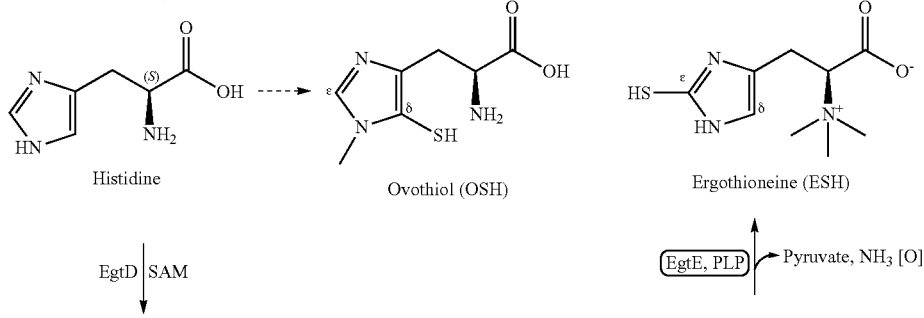

-continued

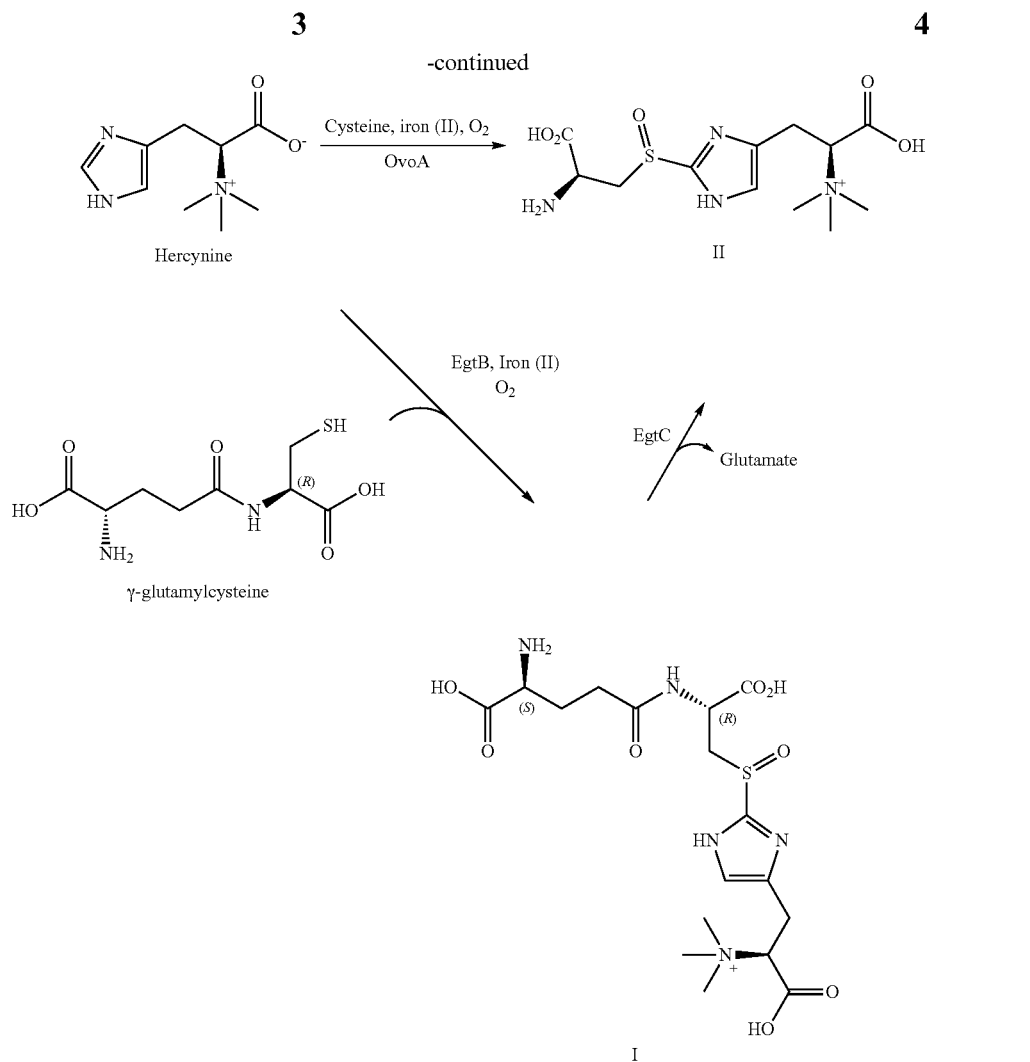

While the enzymes EgtB and EgtC have been expressed in a functional form, EgtE is still elusive and none of the enzymes have been thoroughly studied due to the lack of readily available substrate intermediates.

Recent commercial interest in ESH as a super anti-oxidant molecule has added even greater value to synthetic process development of this molecule. However, known synthetic processes for synthesizing ESH have only been able to achieve low to moderate yields at a very high cost. There is thus still a need to improve the process for synthetically producing ESH.

SUMMARY OF THE INVENTION

According to a first embodiment of the invention, there is provided a process for synthesising a compound of formula V wherein:

n is 0, 1 or 2; and

R is H or

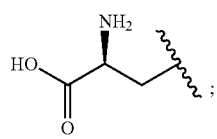 [SMILES: *C[C@H](N)C(=O)O]

or a physiologically acceptable salt, tautomer, stereoisomer or mixture of stereoisomers thereof, the process comprising the steps of:

a) deprotecting a N-benzyl protected histidine of formula 11 to form N-benzyl histidine of formula 12

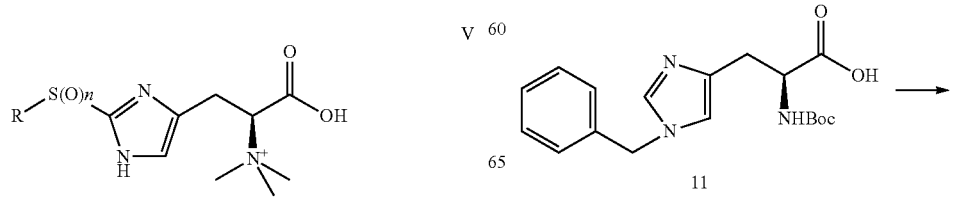

-continued

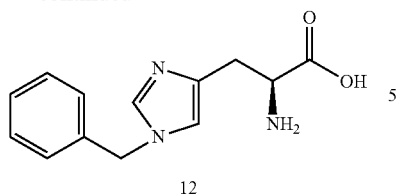

12 b) converting compound 12 to (S)-3-(1-benzyl-1H-imidazol-4-yl)-2-(dimethylamino)propanoic acid of formula 13

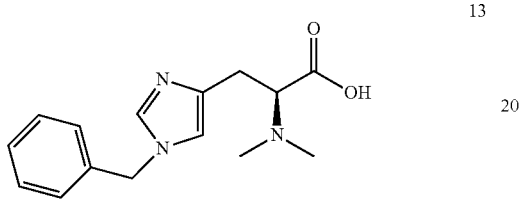

13 c) converting compound 13 to (2S)-N,N,N-2-trimethylethanaminium-3-(1-benzyl-1H-imidazol-4-yl)propanoic acid of formula 14

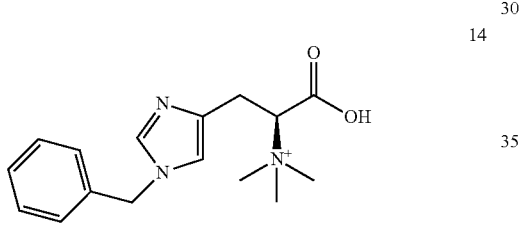

14 d) brominating the imidazole ring of the compound of formula 14 to form 5-bromohercynine lactone; and

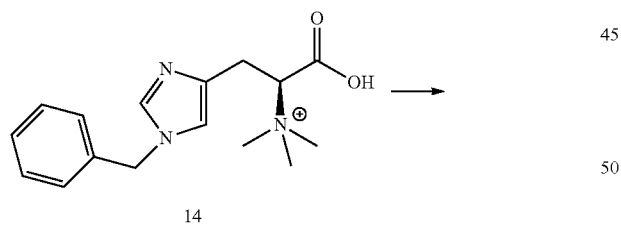

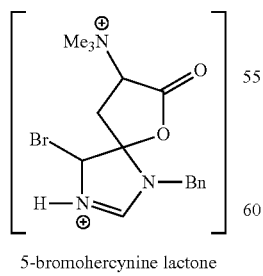

5-bromohercynine lactone e) converting the 5-bromohercynine lactone of step (d) to (β-amino-β-carboxyethyl)ergothioneine sulfide of formula 15

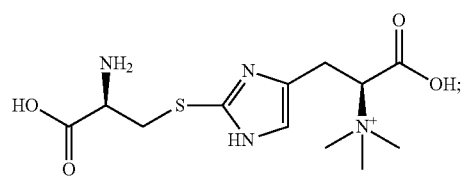

15 wherein the process optionally further includes any one of steps (f) to (h):

f) converting the compound of formula 15 to a sulfoxide of formula II

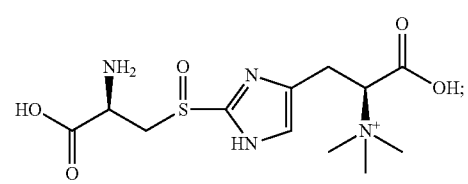

II or g) converting the compound of formula 15 to a sulfone of formula III

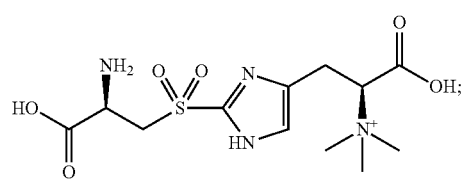

III or h) converting the compound of formula 15 to ergothioneine (ESH) of formula IV

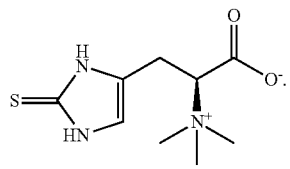

IV

For example,
when n is 0;
R may be

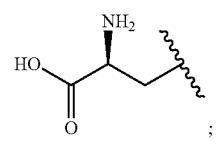

;

or
when n is 1;

R may be

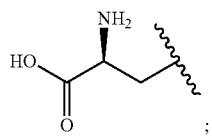

or
when n is 2;
R may be

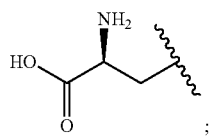 [SMILES: *C[C@H](N)C(=O)O]

or
when n is 0;
R may be H.

The compound of formula V may be selected from the group consisting of:

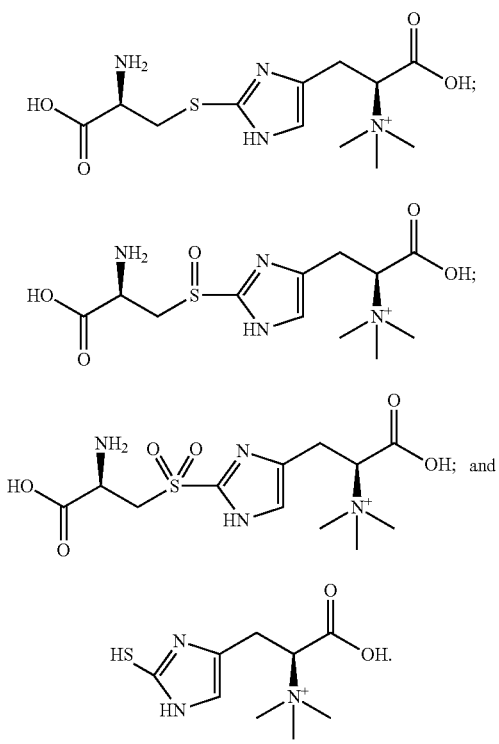

The compound of formula 11 may be a N$^{\alpha}$-Boc-N(im)-benzyl protected L-histidine.

In step (d), dimethylformamide (DMF) and N-bromosuccinimide (NBS) may be used to form the 5-bromohercynine lactone. At least 2 mol equivalents, and preferably at least 2.5 mol equivalents, of NBS relative to compound 14 may be used. Prior to performing step (e), the 5-bromohercynine lactone may be isolated from other products formed in step (d), such as 2.5-bromohercynine.

In step (e), cysteine or thioacetic acid may be used to form the compound of formula 15.

Steps (d) and (e) may be performed together in one-pot synthesis.

In step (h), pyridoxal-5 phosphate (PLP) may be used to form the ergothioneine of formula IV.

After step (f), the sulfoxide of formula II may be further converted to ergothioneine of formula IV. The sulfoxide of formula II may be contacted with an enzyme encoded by the egtE gene, and preferably the EgtE enzyme, to form the ergothioneine of formula IV.

The sulfide of formula 15 formed in step (e), or any one of the intermediate compounds formed in the process, such as 5-bromohercynine, may be labelled with a stable isotope, for example deuterium. The labelled compound or intermediate may be for use in the study of the biosynthesis pathway of ergothioneine or as an internal standard in the quantitation of pathway metabolites during external stimuli or drug treatment.

According to a second embodiment of the invention, there is provided a process for synthesising ergothioneine (ESH) of formula IV or a physiologically acceptable salt thereof, a tautomer, a stereoisomer or a mixture of stereoisomers

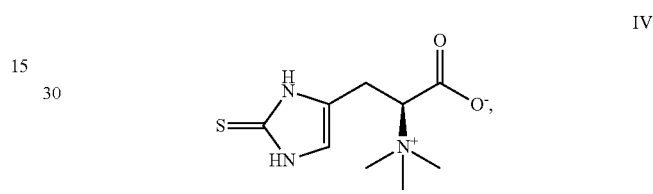

the process comprising the step of contacting a compound of formula 15 with an enzyme encoded by the egtE gene

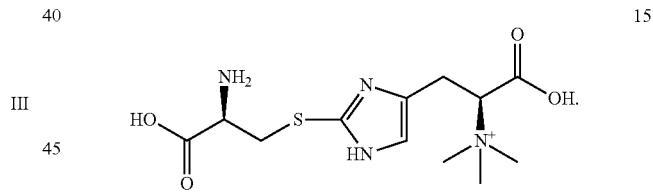

For example, the compound of formula 15 may be contacted with a crude enzyme extract of *M. smegmatis* or EgtE.

According to a third embodiment of the invention, there is provided a process for synthesising ergothioneine (ESH) of formula IV or a physiologically acceptable salt thereof, a tautomer, a stereoisomer or a mixture of stereoisomers

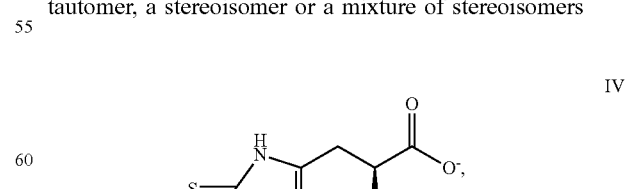

the process comprising the step of contacting a compound of formula 15 with pyridoxal phosphate

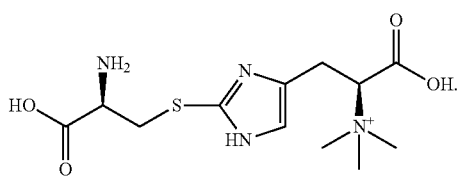

15

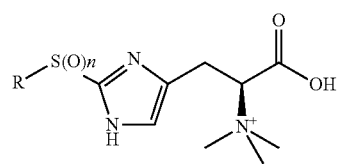

V wherein:
n is 0, 1 or 2; and
R is H or

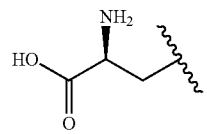 [SMILES: *C[C@H](N)C(=O)O]

(where the wavy line indicates the point of attachment of R to the rest of the molecule of formula V);
or a physiologically acceptable salt, tautomer, stereoisomer or mixture of stereoisomers thereof.

The process utilizes a N-benzyl protected histidine rather than the unprotected form of histidine which is used by known processes of forming compounds of formula V, such as ergothioneine, (β-amino-β-carboxyethyl)ergothioneine sulfide, (β-amino-β-carboxyethyl)ergothioneine sulfoxide and (β-amino-β-carboxyethyl)ergothioneine sulfone.

The process of the invention comprises the steps of:
a) deprotecting a N-benzyl protected histidine of formula 11 to form N-benzyl histidine of formula 12

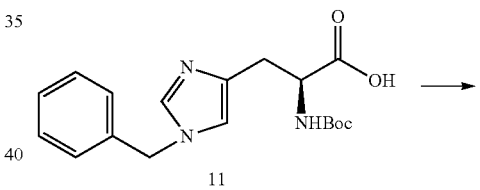

b) converting compound 12 to (S)-3-(1-benzyl-1H-imidazol-4-yl)-2-(dimethylamino)propanoic acid of formula 13

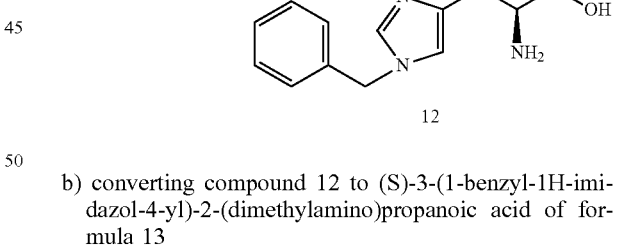

c) converting compound 13 to (2S)-N,N,N-2-trimethyl-ethanaminium-3-(1-benzyl-1H-imidazol-4-yl)propanoic acid of formula 14

DETAILED DESCRIPTION OF THE INVENTION

Figure 1:
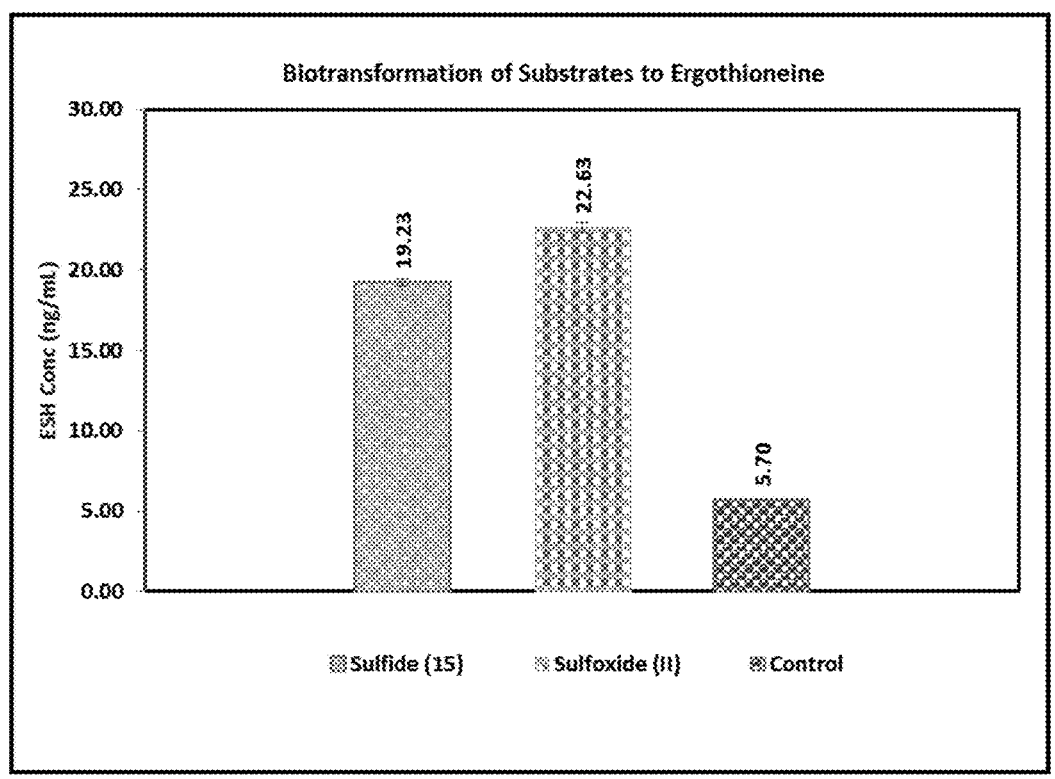
FIG. 1 In vitro reconstitution of ESH; 100 μl reactions containing 20 mM Tris HCl pH=7.4, 20 mM NaCl, 0.2 Mm FeSO$_4$.7H$_2$O, 0.5 mM mercaptoethanol, 83 μl of crude *M. smeg* enzymes and 50 mM of either (a) S-(β-amino-β-carboxyethyl)ergothioneine sulfide (15); (b) S-(β-amino-β-carboxyethyl)ergothioneine sulfoxide (II) and (c) control. The crude enzyme reactions were incubated for 1 day at 37° C. followed by analysis by LC/MS.

The invention provides a process for synthesising a compound of formula V

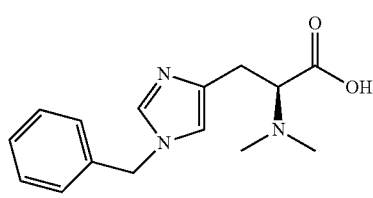

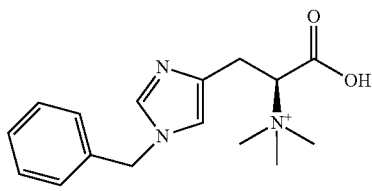

d) brominating the imidazole ring of the compound of formula 14 to form 5-bromohercynine lactone as a reactive intermediate and isolating this 5-bromohercynine derivative (the major product of this reaction) from 2,5-bromohercynine; and

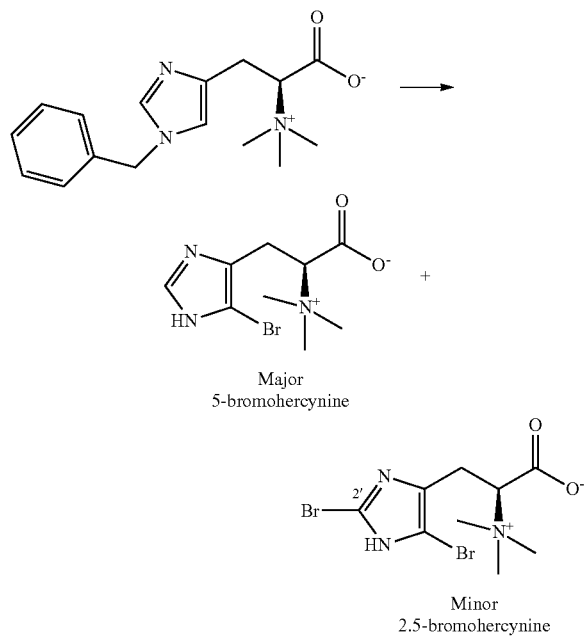

e) converting the 5-bromohercynine lactone of step (d) to (β-amino-β-carboxyethyl)ergothioneine sulfide of formula 15

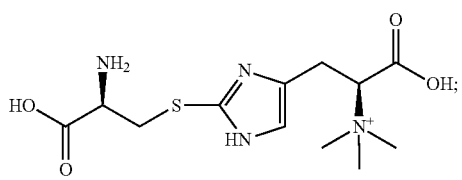

and optionally further includes any one of steps (f) to (h):
f) converting the compound of formula 15 to a sulfoxide of formula II

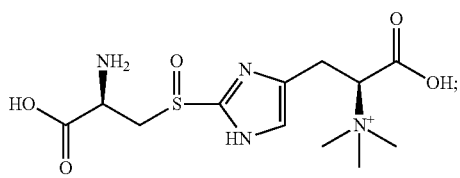

or
g) converting the compound of formula 15 to a sulfone of formula III

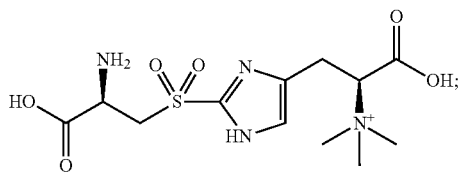

or
h) converting the compound of formula 15 to ergothioneine (ESH) of formula IV

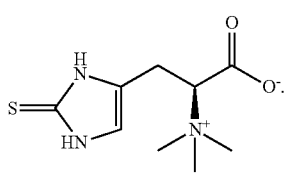

A suitable N-benzyl protected histidine is commercially available from Sigma-Aldrich under the trade name Nα-Boc-N(im)-benzyl-L-histidine. Alternatively, the process may include a step of forming a suitably blocked histidine.

Bacteria, and in particular *mycobacteria* (or enzymatic extracts therefrom) can be used to enzymatically produce the ergothioneine from the synthetically produced S-(β-amino-β-carboxyethyl)ergothioneine sulfide or S-(β-amino-β-carboxyethyl)ergothioneine sulfoxide (II). Suitable bacteria produce the EgtE enzyme and include *Claviceps purpurea*, *Neurospora crassa* and *Mycobacterium smegmatis*.

The ergothioneine produced according to the process of the invention can be used as a neutraceutical, cosmeceutical, hair care product, product to assist with recovery after sport and so forth. The product can be formulated for topical application or oral administration. The sulfone of formula III may be used as an inhibitor of ergothioneine synthesis or in identifying or designing an inhibitor in the ergothioneine synthesis pathway.

Two different routes to the target compound, S-(β-amino-β-carboxyethyl)ergothioneine sulfoxide (II) were attempted by the applicant before the process of the present invention was conceived. In the first approach, retrosynthetic cleavage of S-(β-amino-β-carboxyethyl)ergothioneine sulfoxide (II) gave the β-chloro-alanine methyl ester and ESH (Scheme 2, S1) Thus, S-alkylation of a protected chloromethyl alanine ester (2), derived from serine, provided the core structure (3). The resulting sulfide (3) was oxidised using either mCPBA or $H_2O_2$.

Ishikawa et al. suggested that the reaction may possibly occur via the formation of the cyclic ethylenimine carboxylic acid intermediate produced by an intramolecular $S_N2$ reaction of the β-chloroalanine (2), followed by the ring opening induced by nucleophilic attack of the sulfur atom of ESH, giving the major product N-Boc methyl ester (3a).

Sulfoxidation reaction conditions with $H_2O_2$ previously investigated by Ishikawa et al led to an over oxidation to the sulfone (III) in the applicant's experiments and no analytical evidence was provided. In order to prevent over oxidation of the sulfoxide, mCPBA was used. Its milder nature and potential for controlled sulfoxidation compare to hydrogen peroxide is advantageous. The sulfide methyl ester (3a) was subjected to S-oxidation using one equivalent of mCPBA to afford the sulfoxide methyl ester (4a). The synthetic product is most likely a mixture of $R_cS_s$ and $R_cR_s$ diastereomers. The lowest steric energy conformations (total energy 34.37 kcal/mol) of the sulfide methyl ester (3a) indicated potential face selectivity toward sulfoxidation, which could lead predominantly to the $S_R$ diastereoisomer sulfoxide derivative. $^1$H NMR spectra of the sulfoxide methyl ester (4b) displayed evidence of diastereoselectivity (ca. 3:1 ratio). However, only a crystal structure, supported by CD (circular dichroism) spectra, will help establish the absolute configuration of the major chiral sulfoxide and also that of the natural sulfoxide (II). Deliberate oxidation of sulfide (3b), (4b) or sulfoxide (5a) to the sulfone (III) was achieved with excess oxidant.

Finally, attempted global deprotection of the Boc group and hydrolysis of the methyl ester under aqueous acidic conditions gave only the methyl ester sulfide (3b) or methyl ester sulfoxide (4b) from (3a) and (4a), respectively. Unsuccessful acid, base or esterase mediated ester hydrolysis obligated reconsideration of the synthetic route. Stable amino acid methyl esters have been reported before.[17,18] An allyl ester derivative of β-chloroserine provided the N-Boc allyl ester sulfide (3c) after S-alkylation. Sulfoxidation followed by mild RhCl(PPh$_3$)$_3$ catalysed allyl ester cleavage[19] and acid mediated Boc protecting group removal gave the target S-(β-amino-β-carboxyethyl)ergothioneine sulfoxide (II) in a moderate overall yield of 63%.

With the second retrosynthetic approach, cleavage of the histidine moiety of S-(β-amino-β-carboxyethyl)ergothioneine sulfoxide (3) gave cysteine and bromohercynine derivative (Scheme 2). This route has received the most attention as it provides the required sulfurization of histidine to provide the commercially important ESH. S-(β-amino-β-carboxyethyl)ergothioneine sulfide (5a) was synthesized via a slightly modified Erdelmeier method[20] (Scheme 2). However, a large quantity of salt by-product had to be removed, which hampered purification. Treatment of the S-(β-amino-β-carboxyethyl)ergothioneine sulfide (5a) with 3-mercaptopropionic acid at 90° C. for 18 hr gave ESH. The conversion of the sulfide (5a) to the bis-benzyloxy N-Boc protected ester (5b) allowed organic extraction and removal of salts to give a clean benzyl ester (5b). Global deprotection of the N-Boc benzyl ester (5b) was achieved by hydrogenation (Pd/C) in the presence of TFA under 50 psi hydrogen pressure to give pure S-(β-amino-β-carboxyethyl)ergothioneine sulfide (5a). Biphasic sulfoxidation of the sulfide (5a) with mCPBA in a DCM/water mixture gave the S-(β-amino-β-carboxyethyl)ergothioneine sulfoxide (II) in a low overall yield of 36%.

Scheme 2

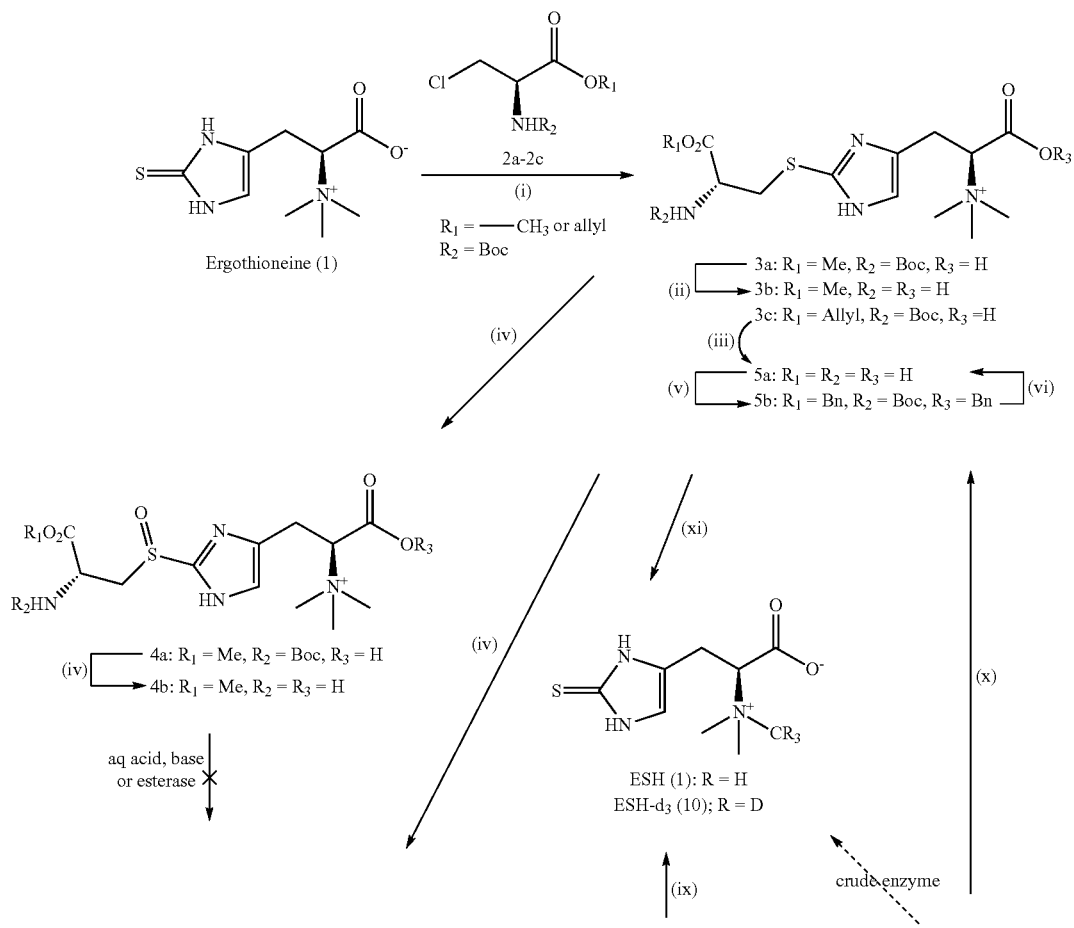

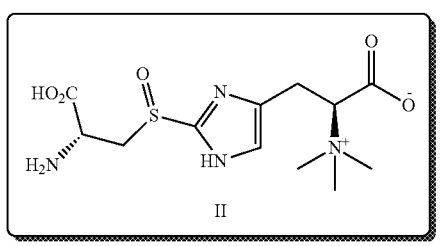

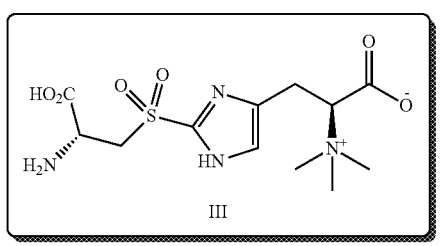

Reagents and conditions: (i) Et₃N/H₂O 5 h at 30° C., (3a); (ii) N-Boc deprotection: TFA, DCM/H₂O, 0-5° C. (3b), (4b) or (II) (iii) a) RhCl(PPh₃)₃, EtOH/H₂O (1:1) reflux b) TFA, DCM/H₂O, 0-5° C. (5a); (iv) mCPBA, H₂O/DCM 1:1, 5 hr at 25° C. (4a) or (II) (v) a) Boc₂O/NaOH, H₂O/CH₃CN, rt overnight b) BnBr/DMF, rt overnight (vi) Pd/C, 3 eq TFA, H₂ 50 psi, rt 12 h; H₂O₂, 3 hr at rt (vii) a) CH₂O, sodium triacetoxyborohydride/ CH₃CN, 18-24 hrs at rt (6), b) NH₄OH, CH₃I or CD₃I/MeOH, 24 h at rt, (7); (viii) a) t-BuOH/HCl, refluxed for 3-4 hrs, S-t-butyl mercaptohistidine; b) CH₂O, sodium triacetoxyborohydride/THF, 6-8 hrs at 10° C., (9); (ix) a) NH4OH, CD₃I/MeOH 24 h, rt; b) HCl, 2-mercaptoprionic acid refluxed for 21 h (quantitative); (x) Br₂, Cysteine HCl, H₂O 1 hr at 0° C., (5a); (xi) 3-mercaptopropionic acid, HCl/H₂O, 19 hrs reflux.

Process for the Synthesis of ESH According to the Invention

The applicant has found that bromination of the N-benzyl protected hercynine intermediate with one equivalent of N-bromosuccinimide (NBS) provides a more stable N-benzyl deprotected 5-bromohercynine lactone derivative using DMF as solvent, in 90% yield (w/w). The success of this method lies in the regioselective C-5 bromination as compared to other known methods. More surprisingly, however, is that when two mol equivalents of the NBS reagent relative to the reactant is utilized, an unprecedented deprotection of the N-benzyl group takes place, resulting in a new in situ deprotection of the N-benzyl group. When proceeding via this latter intermediate, subsequent process steps are near quantitative, relatively simple, all at room temperature, shortened and allow an overall synthesis yield of 80% (w/w). Thus, the process of the invention is capable of providing an overall yield which is at least 2 times better than any prior published process. The final step can be achieved in either chemical, biosynthetic or microbial means. The chemical transformation involves a pyrolytic C—S cleavage.[20] Alternatively, biomimetic pyridoxal phosphate (PLP) mediated cleavage of the sulfide or sulfoxide substrates as well as with crude enzymatic extracts of *M. smegmatis* gave ESH. (Schemes 3 and 4).

Scheme 3.
Improved synthesis of sulfoxide (II), sulfone (III) and ESH: (i) TFA, DCM, rt overnight; (ii) CH₂O, NaBH(OAc)₃, CH₃CN, 24 h at rt; (iii) MeI, THF, 24 h at rt; (iv) (a) NBS (2.5 eq), DMF, dark at rt, b) L-Cysteine HCl• H₂O (2.5 eq), DMF, 24 h at rt; (v) p-toluene sulfonic acid (cat), H₂O₂ (2.4 eq); (vi) boric acid (cat), H₂O₂ (4.8 eq); (vii) C-S enzyme lyase or PLP non enzymatic cleavage.

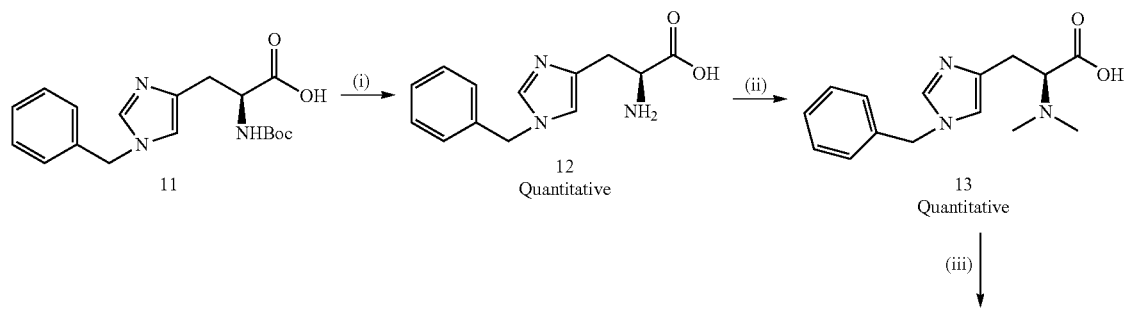

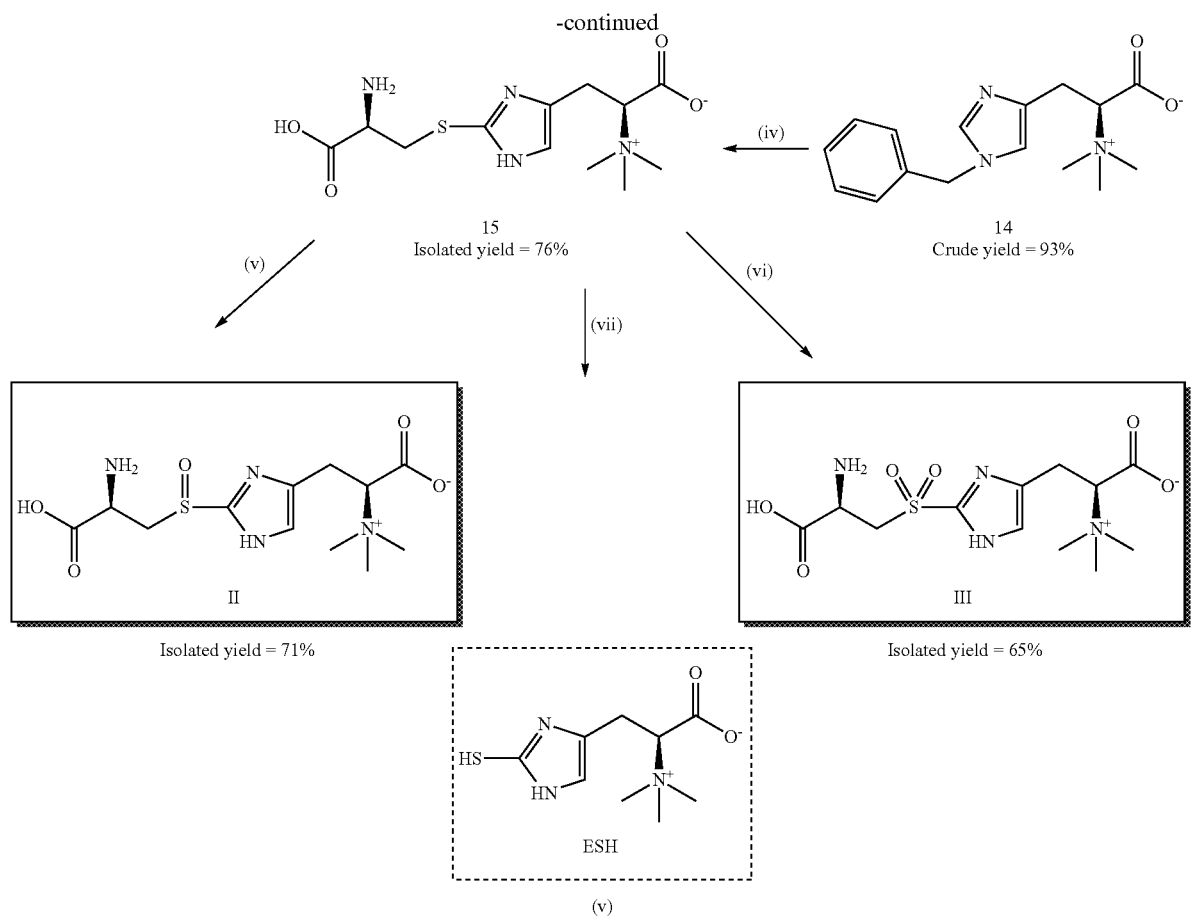

15
Isolated yield = 76%

14
Crude yield = 93%

II
Isolated yield = 71%

III
Isolated yield = 65%

ESH

Scheme 4: Process of the invention using thioacetic acid instead of cysteine

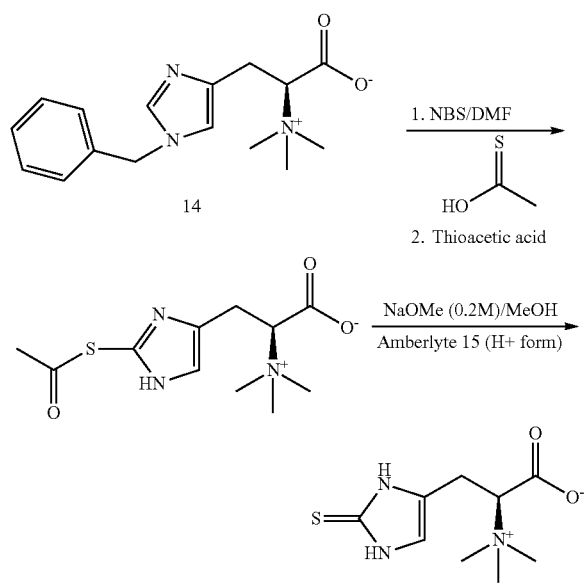

The enzymatic and non-enzymatic PLP mediated synthesis of ESH from the synthetic sulfoxide (II) was compared. To this end, crude M. smegmatis cell free extracts were isolated from cultures grown and harvested at the late exponential phase, characterised by high enzymatic activity.[10]

The crude enzymatic transformation of the ESH biosynthetic pathway precursors, including sulfide and sulfoxide variants were evaluated by the concomitant production of ESH in excess of basal levels as determined by LCMS. ESH precursor metabolites (β-amino-β-carboxyethyl)ergothioneine sulfide (15) and (β-amino-β-carboxyethyl)ergothioneine sulfoxide (II) were incubated with the crude cell free extract at 37° C., pH=7.4 for 1 day, and analyzed by LCMS.

The control reaction containing only the crude M. smegmatis cell free extract was also treated under the same conditions as the metabolites. The concentration of ESH thus obtained was 5.70 (±0.30) ng/ml, which was equated to that of endogenous ESH. This concentration was above the limit of detection (0.78 ng/ml), thus any increase in the concentration of ESH in the experiment above 1 ng/ml is considered significant enough to be ascribed to basal levels or biotransformation of the respective substrates by the crude endogenous enzymes of the ESH pathway.

Figure 2:
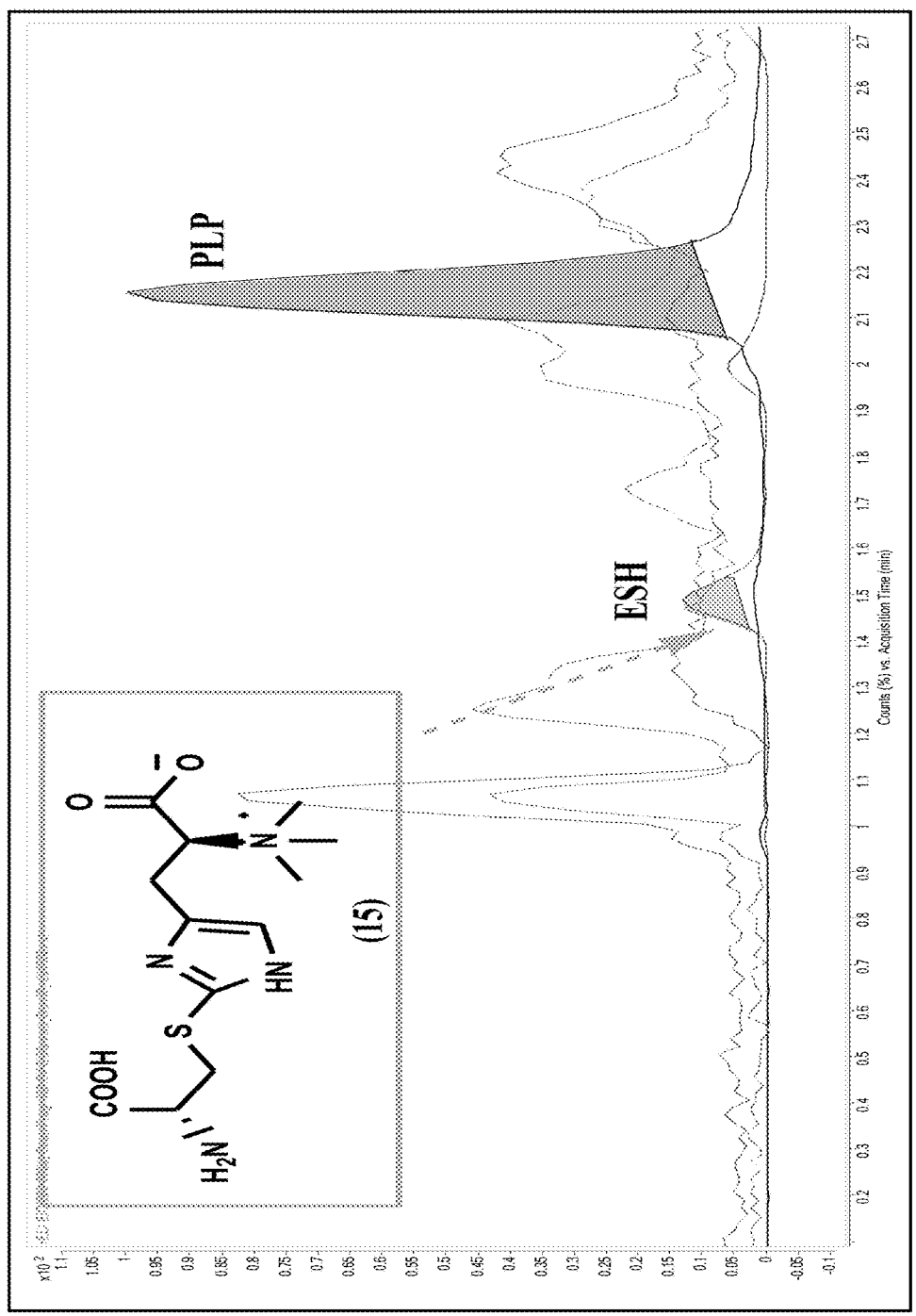
FIG. 2 Non enzymatic production of ESH catalysed by PLP. TIC extracted for ESH and PLP using S-(β-amino-β-carboxyethyl)ergothioneine sulfide (15), S-(β-amino-β-carboxyethyl)ergothioneine sulfoxide (II) and S-(β-amino-β-carboxyethyl)ergothioneine sulfone (III). Only S-(β-amino-β-carboxyethyl)ergothioneine sulfide (15) produced significant amount of ESH (96.34 ng/mL) while sulfoxide (II) and sulfone (III) did not produce ESH at all.
Figure 3:
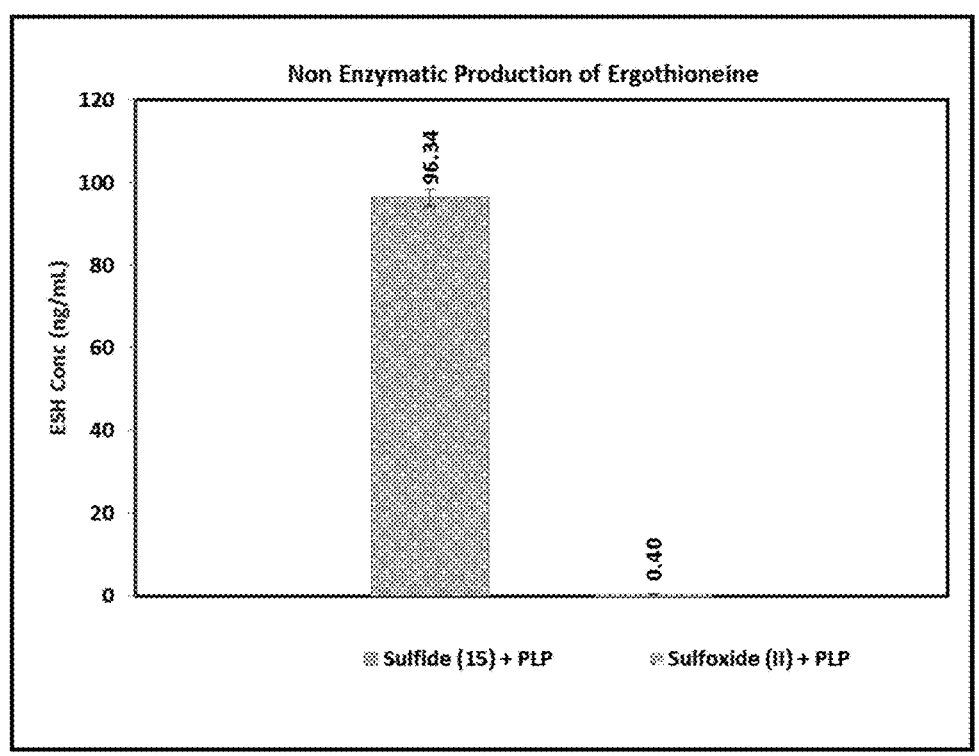
FIG. 3 Non enzymatic production of ESH graph contain; 100 μl reactions containing 20 mM Tris HCl pH=7.4, 20 mM NaCl, 50 mM of either (1) sulfide (15) plus PLP, (2) sulfoxide (II) plus PLP, (3) sulfone (III) plus PLP respectively. Reaction time: 24 h.

(β-amino-β-carboxyethyl)ergothioneine sulfoxide (II) biosynthetically produced the highest concentration of ESH (22.6 ng/ml) (FIG. 1). The (β-amino-β-carboxyethyl)ergothioneine sulfide (15) appeared to be almost as good a substrate as the (β-amino-β-carboxyethyl)ergothioneine sulfoxide (II) (19.2 ng/ml ESH). It is well known that PLP-dependent transformations can undergo enzyme free conversion albeit with a much slower rate and specificity.[22] Thus, the non-enzymatic treatment of the sulfide (15) with 50 mM PLP at 37° C. resulted in an efficient formation of ESH (96.3 ng/ml) (FIG. 2). However, under the same conditions, the sulfoxide (II) produced no ESH at all (FIG. 3).

The increased yield which is obtained by the process of the invention will also allow intermediates to be recovered in higher quantities for isotopic labelling. The high yields of the intermediate products also allow viable isotopic labelling steps to be performed. Isotopes are usually very expensive and are advantaged by high yield conversions.

Previously, radiolabeled intermediates have been used to elucidate the biosynthesis pathway of ESH. The applicant has now found that it is possible to synthesize the same intermediates incorporating stable isotopes, and the synthesis of ESH-$d_3$ (10) from deuterated hercynine is described in more detail below.

These intermediates with stable isotope labels can be used, for example, for further study of the ESH pathway or as internal standards in the quantitation of pathway metabolites during external stimuli or drug treatment.

It is envisaged that the S-(β-amino-β-carboxyethyl)ergothioneine sulfone, which as mentioned earlier is stable to the Egt E enzyme mediated C—S cleavage, could serve as an inhibitor of ESH synthesis or be useful in designing or screening other inhibitors of enzymes in the ESH pathway (in particular Egt E). Inhibitors of ESH biosynthesis enzymes may lead to the development of new protein targets and the development of drugs for making M. tuberculosis more sensitive to treatment regimes.

The invention will now be described in more detail by way of the following non-limiting examples.

EXAMPLES

1. General Procedures

All solvents were dried by appropriate techniques and freshly distilled before use. All commercially available reagents were purchased from Sigma-Aldrich and Merck and were used without further purification.

Unless otherwise stated, reactions were performed under an inert atmosphere of nitrogen in oven dried glassware and monitored by thin-layer chromatography (TLC) carried out on Merck silica gel 60-$F_{254}$ sheets (0.2 mm layer) pre-coated plates and products visualized under UV light at 254 nm or by spraying the plate with an ethanolic solution of ninhydrin (2% v/v) followed by heating.

Column chromatography was effected by using Merck Kieselgel silica gel 60 (0.040-0.063 mm) and eluted with an appropriate solvent mixtures. All compounds were dried under vacuum before yields were determined.

Nuclear magnetic resonance spectra $^1$H and $^{13}$C) were recorded on a Varian Mercury 300 MHz (75 MHz for $^{13}$C), Varian Unity 400 MHz (101 MHz for $^{13}$C), a Bruker unity 400 MHz (101 MHz for $^{13}$C), or a Bruker unity 600 MHz (151 MHz for $^{13}$C) and were carried out in $CDCl_3$, DMSO-$d_6$ and $D_2O$ as the solvent unless otherwise stated. Chemical shifts are given in ppm relative to tetramethylsilane (TMS, δ=0.00 ppm), which is used as internal standard. Assignments were confirmed by COSY, APT and HSQC analysis, when required. Coupling constants (J) are reported in Hertz (Hz). The spin multiplicities are indicated by the symbol s (singlet), d (doublet), dd (doublet of doublets), t (triplet), m (multiplet), q (quartet) and br (broad).

Optical rotations were obtained using a Perking Elmer 141 polarimeter at 20° C. The concentration c refers to g/100 ml.

Melting points were determined using a Reichert-Jung Thermovar hot-plate microscope and are uncorrected. Infra-Red spectra were recorded on a Perkin-Elmer FT-IR spectrometer (in $cm^{-1}$) from 4000 $cm^{-1}$ to 450 $cm^{-1}$.

Mass spectra were recorded on a JEOL GC MATE II magnetic sector mass spectrometer and the base peaks are given, University of Cape Town.

LCMS analyses were carried out with a UHPLC Agilent 1290 Infinity Series (Germany), accurate mass spectrometer Agilent 6530 Qradrupole Time Of Flight (QTOF) equipped with an Agilent jet stream ionization source (positive ionization mode) (ESI$^+$) and column (Eclipse+$C_{18}$ RRHD 1.8 μm. 2.1×50, Agilent, Germany).

Enzymatic reactions were allowed to incubate in Nuaire incubator (DH Autoflow $CO_2$ Air—jarcketed Incubator), and centrifuged in Eppendhorf centrifuge (Model 5810R, Germany), Tygerberg Stellenbosch University, Cape Town, South Africa.

2. Synthesis of Ergothioneine Substrates and Sulphone

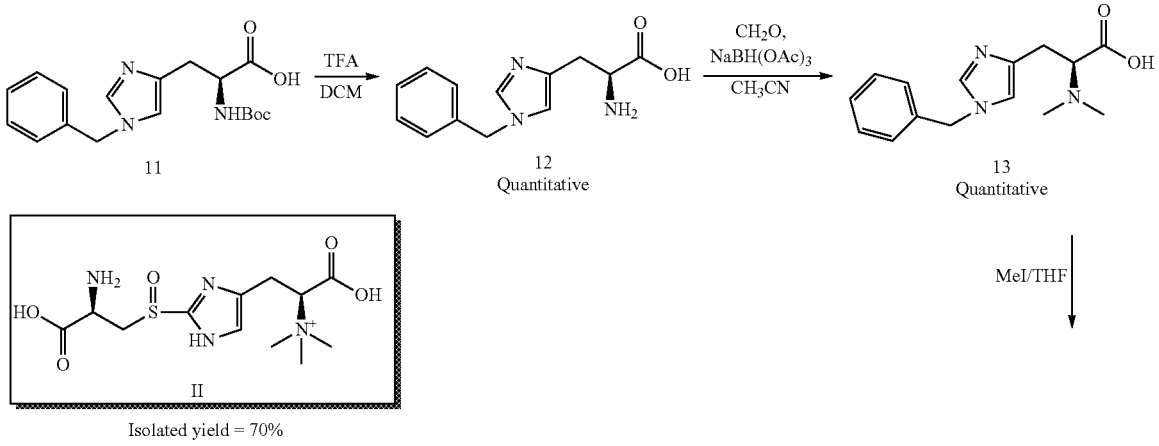

Scheme 5: Synthesis of sulfoxide (II) and sulfone (III)

Isolated yield = 70%

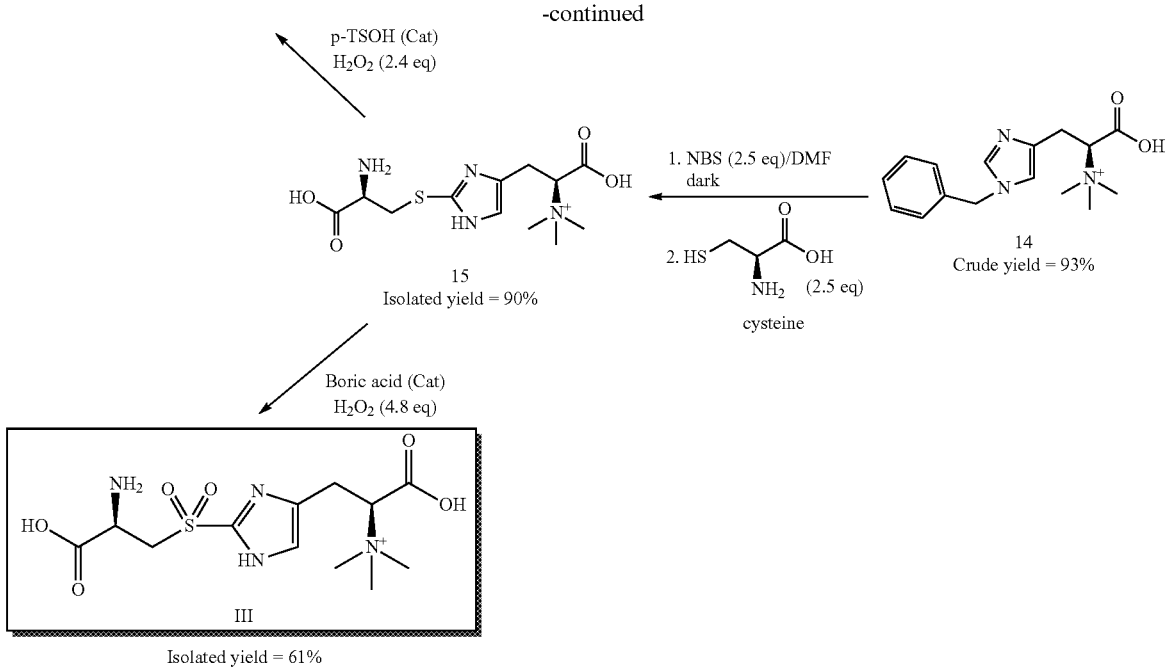

N-benzyl-L-histidine (12)

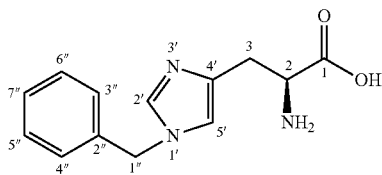 [SMILES: N[C@@H](Cc1cn(Cc2ccccc2)cn1)C(=O)O]

Figure 4:
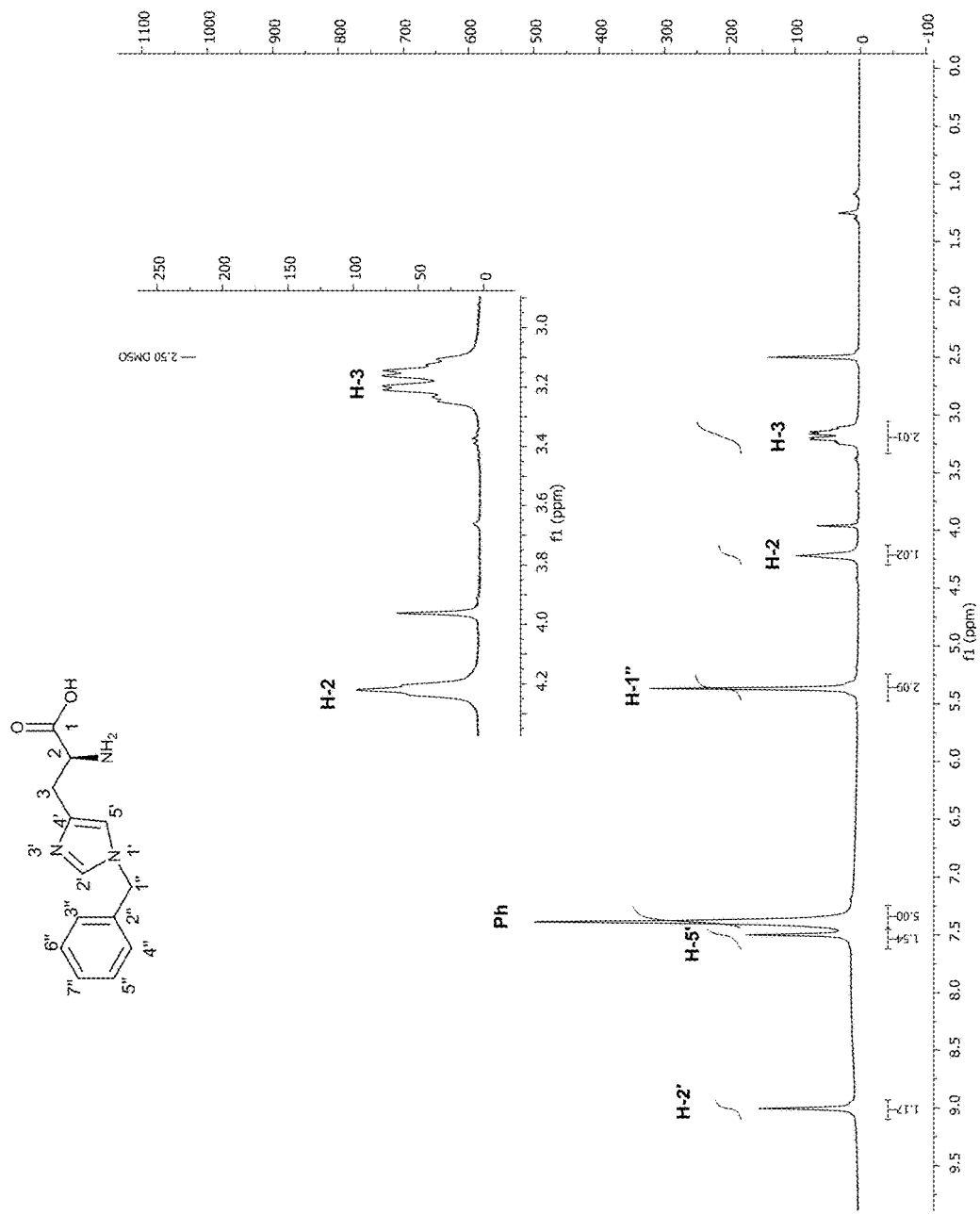
FIG. 4 $^1$H NMR spectrum of (12) in DMSO at 400 MHz.
Figure 5:
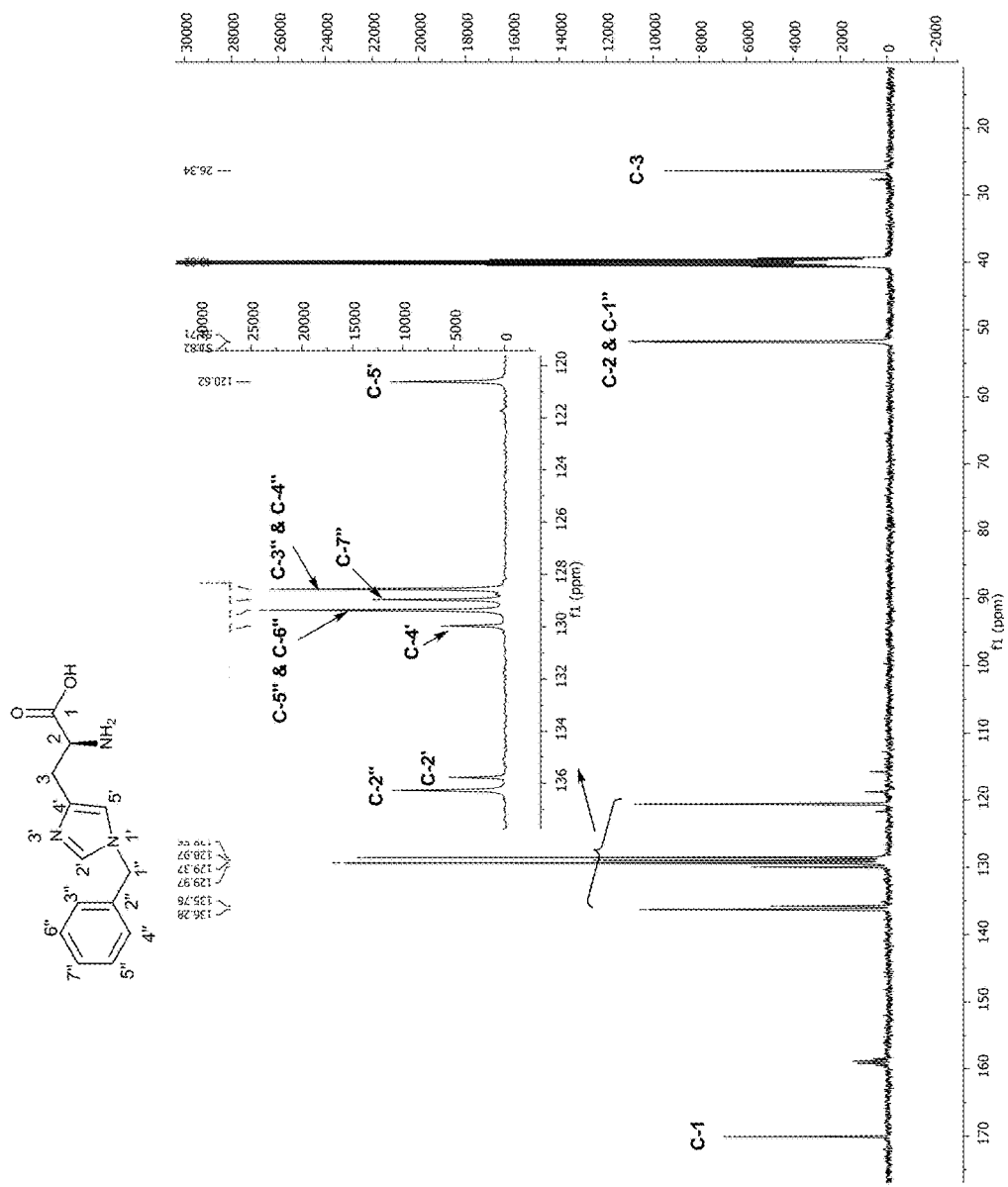
FIG. 5 $^{13}$C NMR spectrum of (12) in DMSO at 101 MHz.

Nα-Boc-N(im)-benzyl-L-histidine 11 (Sigma-Aldrich) (750 mg, 2.17 mmol) was suspended in dichloromethane (10 mL), followed by the addition of trifluoroacetic acid (1 mL) with cooling in an ice bath. The resulting homogenous solution was allowed to stir at room temperature until complete deprotection as showed by thin layer chromatography. Solvent was removed and triturated with $Et_2O$ (15 mL) and dried to afford the product 12 as white crystals (700 mg, quantitative). Mp: 230-233° C., (Lit. 240° C.)[1]; $^1H$ NMR (400 MHz, DMSO) δ 9.01 (s, 1H, H-2'), 7.50 (s, 1H, H-5'), 7.39 (m, 5H, Phenyl), 5.37 (s, 2H, H-1"), 4.22 (t, J=7.0 Hz, 1H, H-2), 3.22 (dd, J=15.6, 7.0 Hz, 1H, H-3a), 3.14 (dd, J=15.6, 7.0 Hz, 1H, H-3b); $^{13}C$ NMR (101 MHz, DMSO) δ 170.1 (C-1), 136.3 (C-2"), 135.8 (C-2'), 130.0 (C-4'), 129.4 (C-5" C-6"), 129.0 (C-7"), 128.6 (C-3"C-4"), 120.6 (C-5'), 51.7 (C-1"), 51.6 (C-2), 26.3 (C-3) (FIGS. 4 and 5).

(S)-3-(1-benzyl-1H-imidazol-4-yl)-2-(dimethylamino)propanoic acid (13)

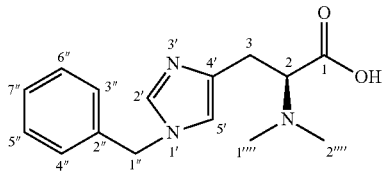 [SMILES: CN(C)[C@@H](Cc1cn(Cc2ccccc2)cn1)C(=O)O]

Figure 21:
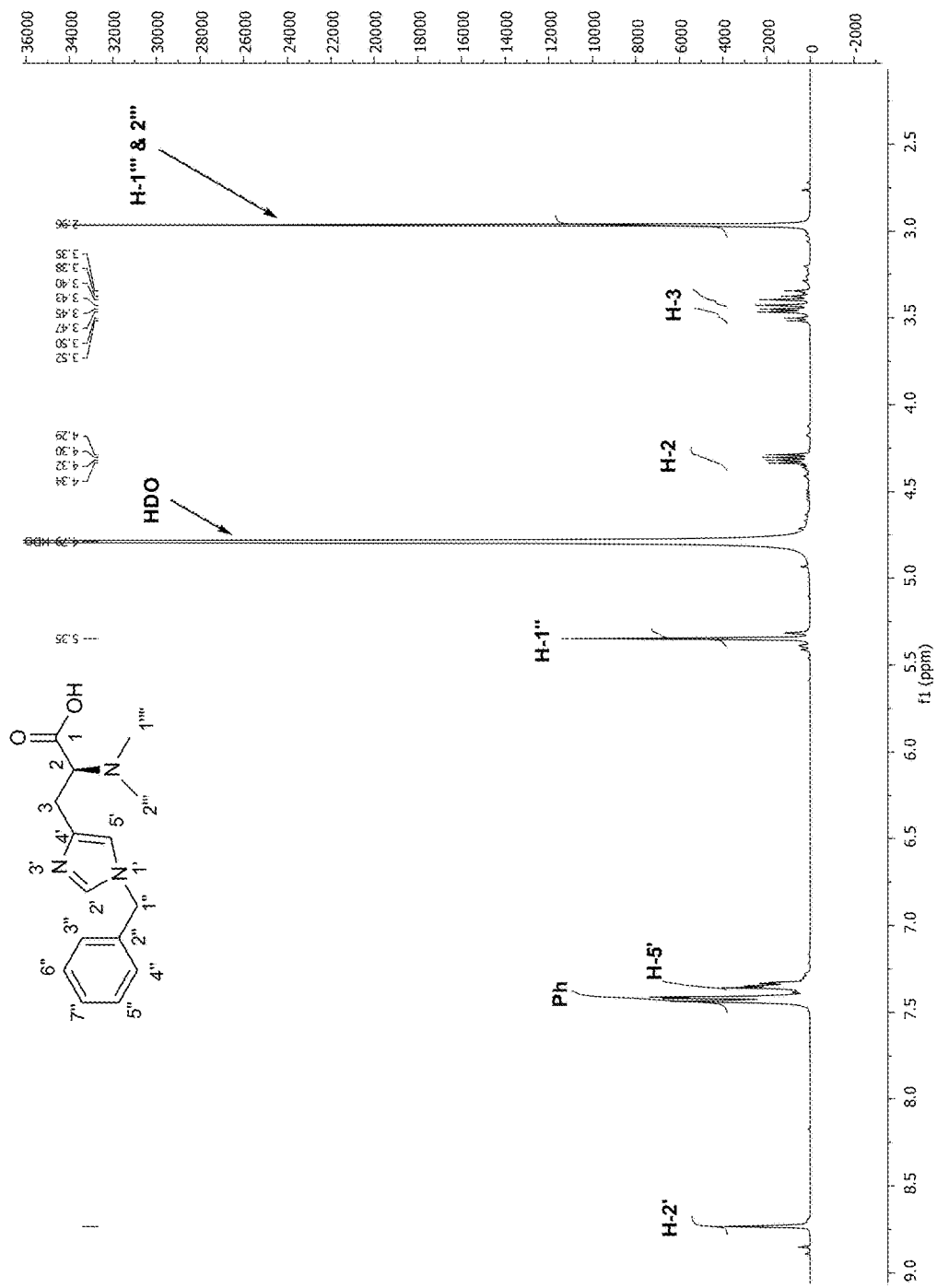
FIG. 21 $^1$H NMR spectrum of (13) in DMSO at 400 MHz.

In $CH_3CN$ (20 mL) was suspended 12 (1.31 g, 5.34 mmol) followed by the addition of formaldehyde (1.2 mL, 15.5 mmol, 37%). To the resulting homogenous solution was added $NaBH(OAc)_3$ (3.2 g, 15.5 mmol) and the solution was allowed to stir at room temperature for 24 hours. Undesirable salts were filtered thought celite and the solvent evaporated to dryness to afford the crude dimethyl product 13 as yellow oil (1.80 g, quantitative). Attempts to isolate this product with a liquid-liquid extraction process were unsuccessful due to the zwitterionic nature of the molecule. However, this product was sufficiently pure and was used in the next step without further purification (FIG. 21).

(2S)-N,N,N-2-trimethylethanaminium-3-(1-benzyl-1H-imidazol-4-yl)propanoic acid (14)

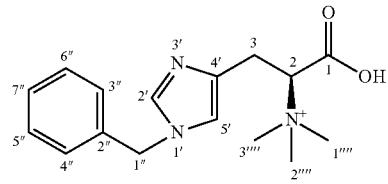

Figure 6:
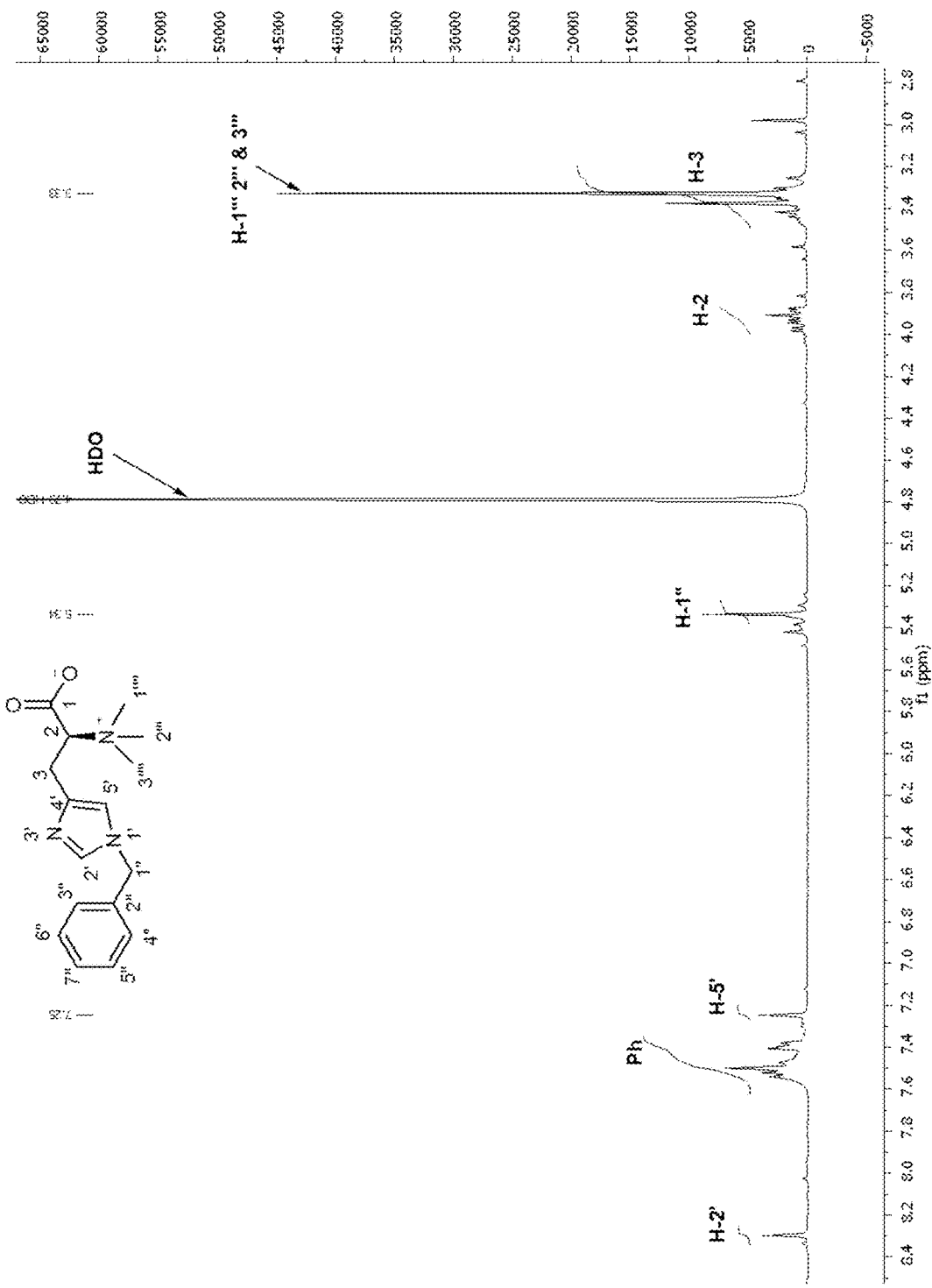
FIG. 6 $^1$H NMR spectrum of (14) in D$_2$O at 400 MHz.
Figure 7:
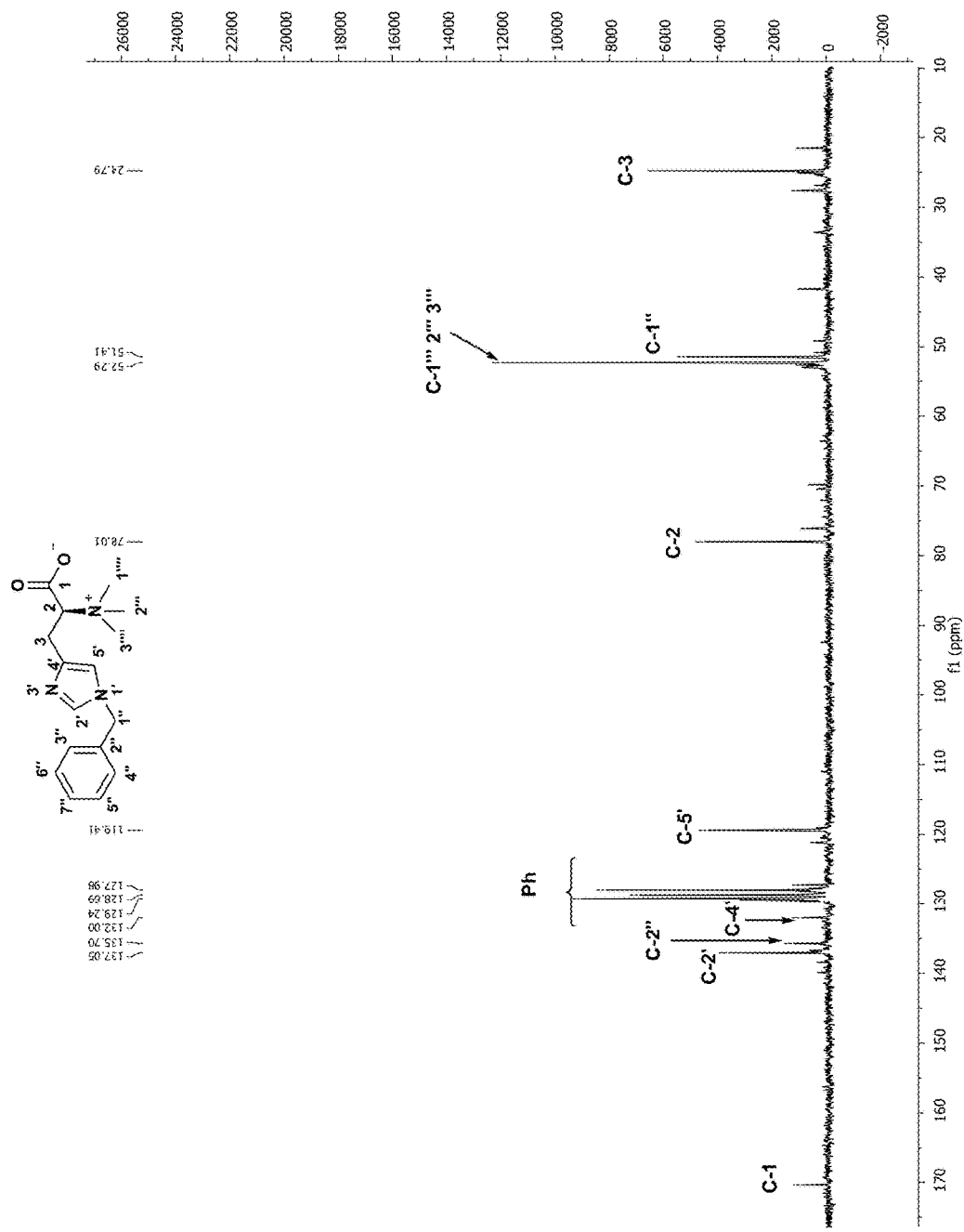
FIG. 7 $^{13}$C NMR spectrum of (14) in D$_2$O at 101 MHz.

In dry tetrahydrofuran (10 mL) was dissolved the crude dimethyl product 13 (870 mg, 3.16 mmol) followed by the addition of MeI (0.41 mL, 942 mg, 6.64 mmol). The resulting solution was allowed to stir at room temperature in the dark for 1-2 days. The solvent was removed to afford the product 14 as a yellow oil (822 mg, 93%). Crystallization in the absolute ethanol afforded product 14 as white solid. Mp: 156° C. (dec), $^1H$ NMR (400 MHz, $D_2O$) δ 8.65 (d, J=1.6 Hz, 1H, H-2'), 7.39-7.29 (m, 5H, Ph), 7.28-7.24 (m, 1H, H-5'), 5.27 (s, 2H, H-1'), 4.26 (dd, J=9.7, 4.7 Hz, 1H, H-2), 3.47-3.36 (m, 2H, H-3), 2.88 (s, 9H, H-1"H-2"H-3"); $^{13}C$ NMR (101 MHz, $D_2O$) δ 169.0 (C-1), 134.9 (C-2'), 134.7 (C-2"), 133.5 (C-4'), 129.3 (C-3" C-4"), 128.4 (C-5" C-6"), 127.5 (C-7"), 121.0 (C-5'), 81.8 (C-2), 65.4 (C-1"), 52.7 (C-1'''C-2'''C-3'''), 21.8 (C-3); LRMS (EI$^+$) m/z calculated for $C_{16}H_{21}N_3O_2$ 287.2 [M-1]$^+$ found 287.1 ([M]$^+$, 1%), calculated for $C_{14}H_{17}N_3^+$ 227.1 [M-$CO_2$ and —$CH_3$]$^+$ found 227.1 ([M-$CO_2$ and —$CH_3$]$^+$, 100%) (FIGS. 6 and 7).

Selective and Mild Bromination of the Imidazole Ring

Scheme 6: Selective and mild bromination of the imidazole ring

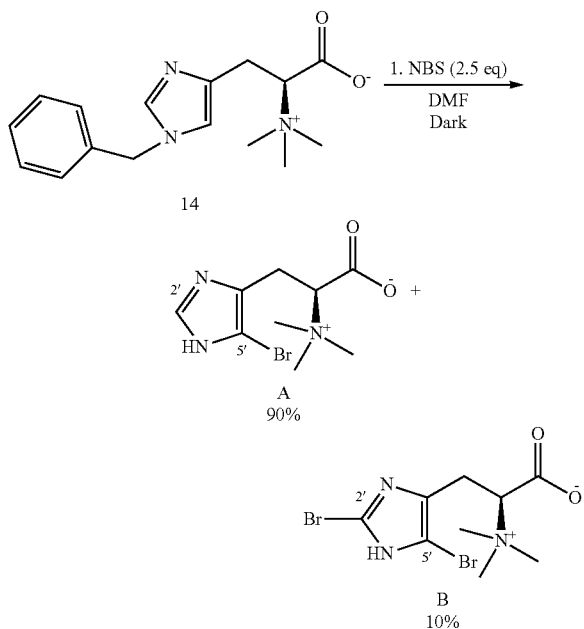

Figure 8:
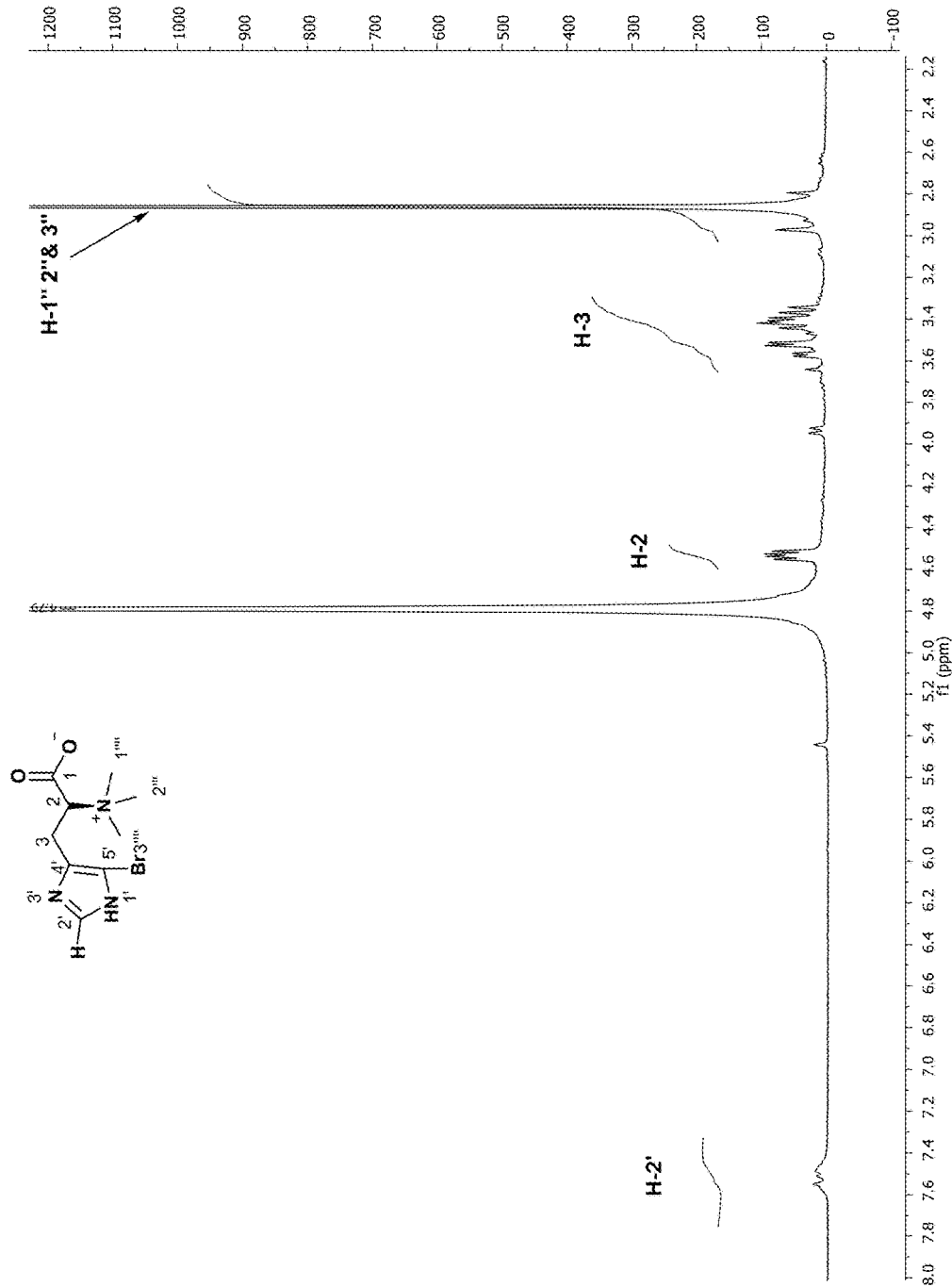
FIG. 8 $^1$H NMR spectrum of (A) in D$_2$O at 300 MHz.
Figure 9:
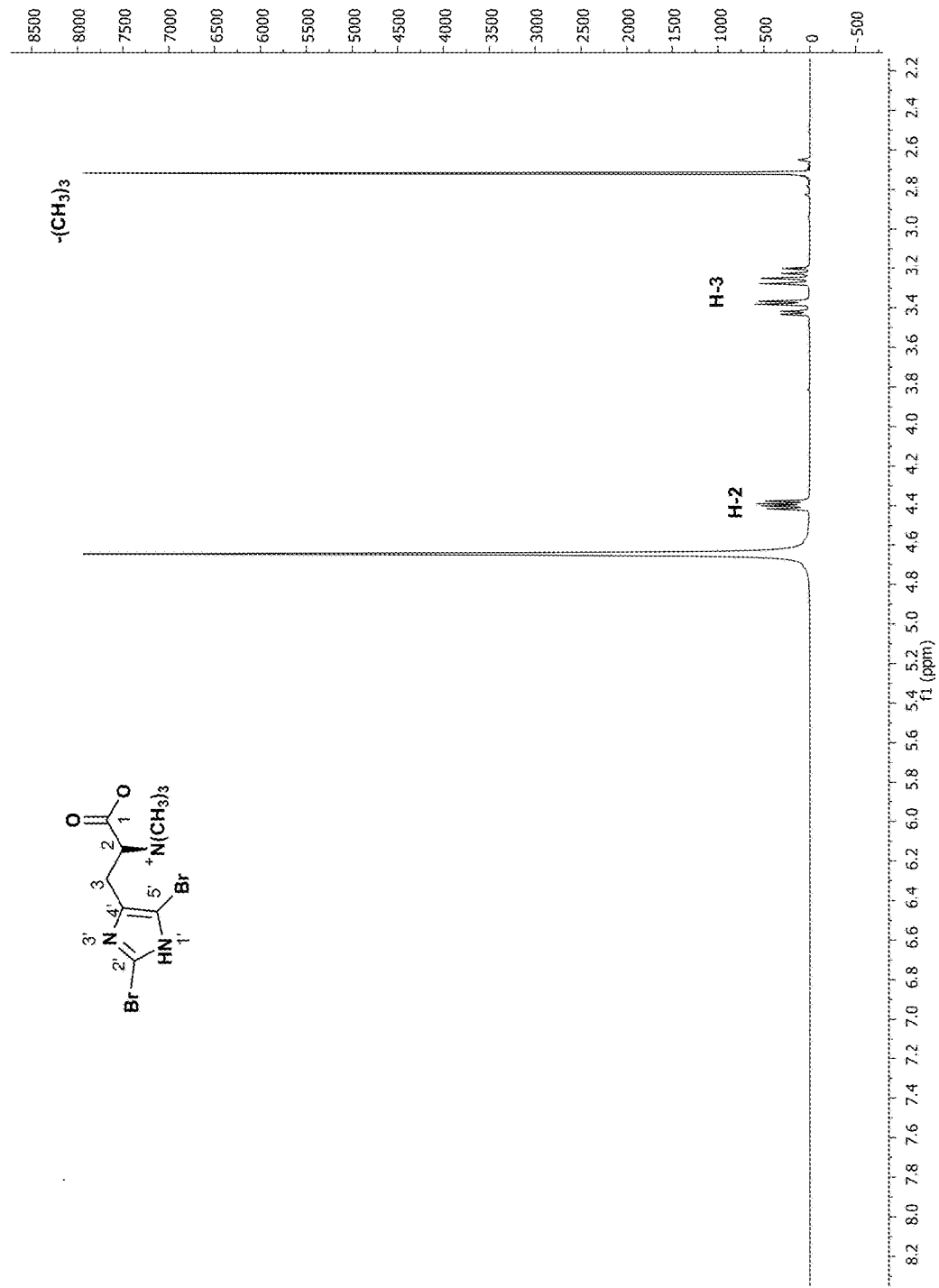
FIG. 9 $^1$H NMR spectrum of (B) in D$_2$O at 300 MHz.

The bromination condition was optimised to be very selective. Two brominated intermediates have been found stable enough to be isolated by reverse phase C18 chromatography. The mono brominated intermediate, 5-bromo hercynine (A) (FIG. 8) was isolated in very high yield (90%), while the 2,-5 dibromo hercynine intermediate (B) (FIG. 9) was isolated in a low yield of 10%.

Hercynyl Cysteine Thioether (15) (One Pot Synthesis)

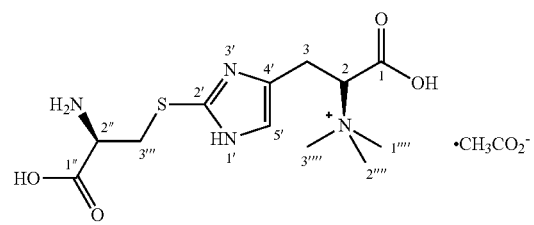

In dimethylformamide (8 mL) was dissolved 14 (700 mg, 2.43 mmol) followed by the addition of N-bromosuccimide (1.8 g, 6.08 mmol). The resulting solution was allowed to stir at room temperature until complete disappearance of the starting material (thin layer chromatography monitoring), the solution became red-orange indicating the successful bromination.

Figure 10:
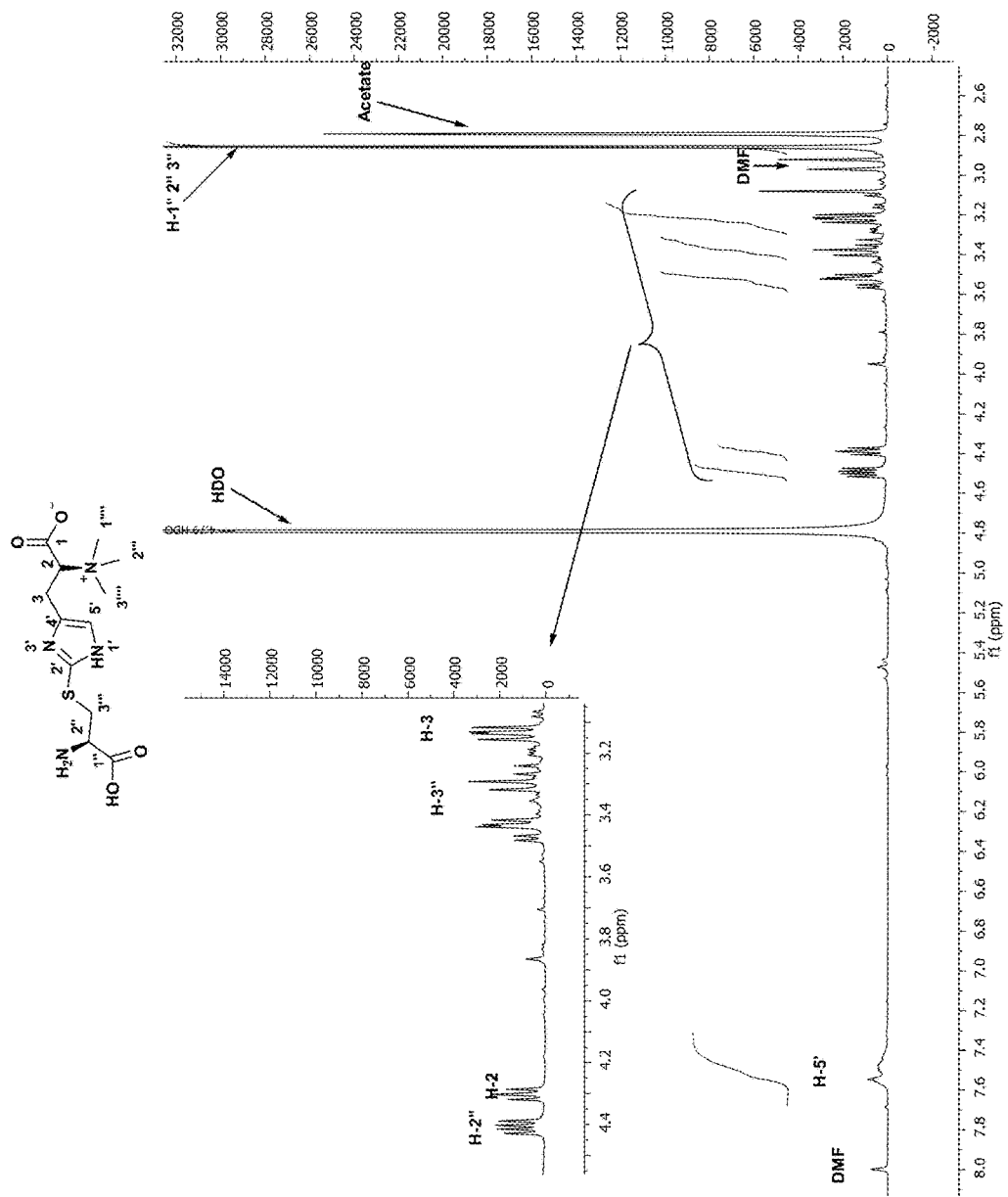
FIG. 10 $^1$H NMR spectrum of (15) in D$_2$O at 400 MHz.

After successful bromination, cysteine HCl. H$_2$O (1.07 g, 6.08 mmol) was added in one portion and the resulting solution was allowed to stir at room temperature for 24 hours. Reverse phase chromatography C18 afforded the product 15 isolated as the yellow hygroscopic solid acetate salt form (695 mg, 90%). $^1$H NMR (400 MHz, D$_2$O) δ 7.41 (m, 1H), 4.54 (dd, J=7.7, 4.4 Hz, 1H, H-2"), 4.42 (t, J=5.0 Hz, 1H, H-2), 3.50 (dd, J=15.2, 4.4 Hz, 1H, H-3a"), 3.36 (dd, J=15.2, 7.7 Hz, 1H, H-3b"), 3.19 (m, 2H, H-3), 2.80 (s, 9H, H-1"'H-2"'H-3"'), 2.75 (s, 3H, acetate); $^{13}$C NMR (101 MHz, D$_2$O) δ 170.3 (C-1"), 170.0 (C-1), 129.4 (C-2'), 128.9 (C-4'), 120.9 (C-5'), 61.0 (C-2), 54.4 (C-2"), 51.7 (C-1"''C-2"''C-3"''), 36.3 (C-3"), 23.9 (C-3); HRMS (ESI$^+$): m/z 317.1284 [M]$^+$. Calculated for C$_{12}$H$_{21}$N$_4$O$_4$S$^+$ found 317.1277 [M]$^+$ (FIG. 10).

Synthesis of Hercynyl Cysteine Sulfoxide (II) and Sulfone (III)

S-(β-amino-β-carboxyethyl)ergothioneine sulfoxide or (2S)-N,N,N-2-trimethylammonium-3-[2-((2R)-2-amino-2-hydroxycarbonyl)ethylsulfinyl)-1H-imidazol-4-yl]propanoic acid (II)[26]

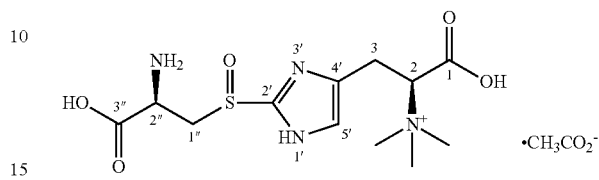

Figure 11:
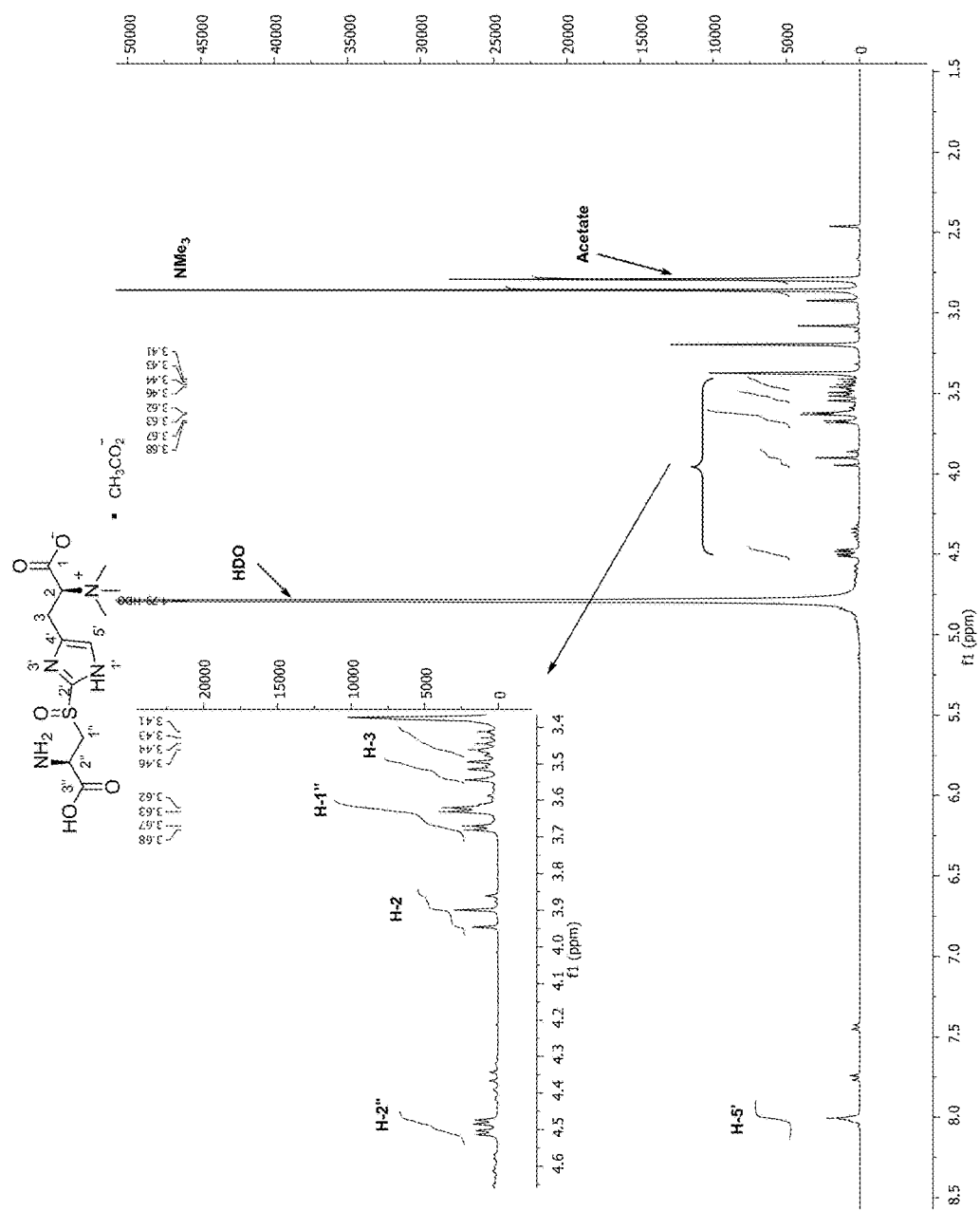
FIG. 11 $^1$H NMR spectrum of (II) in D$_2$O at 300 MHz.

To a solution of H$_2$O$_2$ (30%, 224 mg, 6.58 mmol, 2.4 eq) were added 15 (870 mg, 2.74 mmol) and para toluene sulfonic acid (15 mg, 0.08 mmol). The resulting reaction mixture was allowed to stir at room temperature for 24 hours. At the end the reaction was quenched by the addition of H$_2$O (10 mL) and evaporated under high vacuum to afford crude product, which was purified by C18 reverse phase to afford product II as a yellow solid (640 mg, 70%). $^1$H NMR (300 MHz, D$_2$O) δ 8.01 (s, 1H, H-5'), 4.49 (dd, J=8.6, 3.3 Hz, 1H, H-2"), 3.90 (dd, J=16.1, 9.3 Hz, 1H, H-2), 3.65 (dd, J=15.0, 3.3 Hz, 2H, H-1"), 3.52 (dd, J=9.3, 4.9 Hz, 1H, H-3a), 3.44 (dd, J=9.3, 4.9 Hz, 1H, H-3b), 2.86 (s, 9H, NMe$_3$), 2.79 (s, 3H, acetate); $^{13}$C NMR (101 MHz, D$_2$O) δ 171.8 (C-3"), 170.1 (C-1), 156.6 (C-2'), 129.5 (C-4'), 125.5 (C-5'), 72.5 (C-2), 49.5 (NMe$_3$), 49.1 (C-1"), 43.5 (C-2"), 20.8 (C-3); HRMS (ESI$^+$): m/z 334.1306 [MH]$^+$. Calculated for C$_{12}$H$_{22}$N$_4$O$_5$S$^{2+}$, found 334.1321 [MH]$^+$ (FIG. 11).

S-(β-amino-β-carboxyethyl)ergothioneine sulfone or (2S)-N,N,N-2-trimethylammonium-3-[2-((2R)-2-amino-2-hydroxycarbonyl)ethylsulfonyl)-1H-imidazol-4-yl]propanoic acid (III)[27]

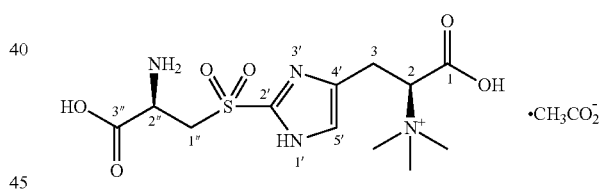

Figure 12:
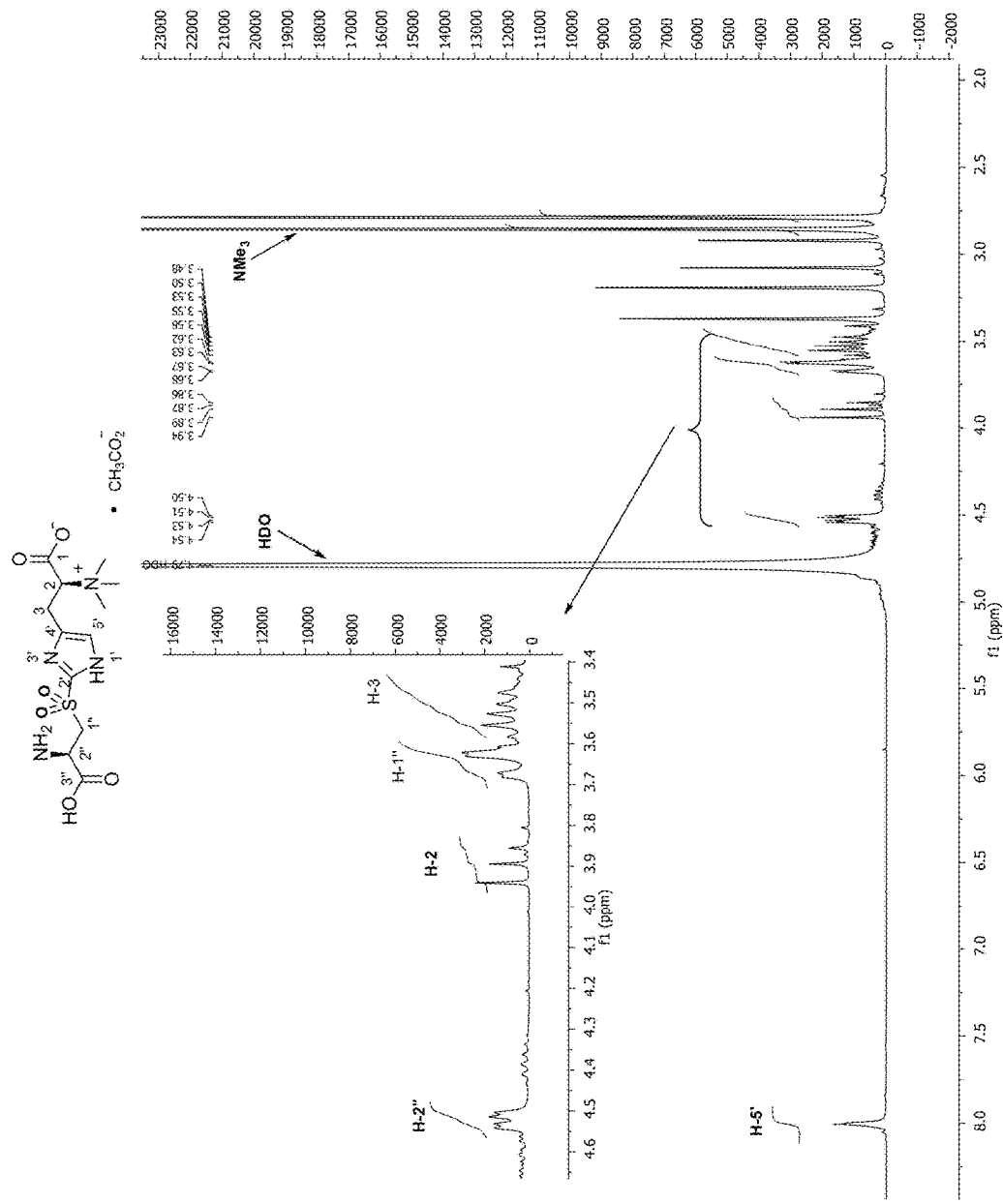
FIG. 12 $^1$H NMR spectrum of (III) in D$_2$O at 300 MHz.

15 (810 mg, 2.55 mmol) was added to a solution of H$_2$O$_2$ (30%, 416 mg, 12.24 mmol, 4.8 eq) and boric acid (5 mg, 0.08 mmol), and the reaction mixture was allowed to stir at room temperature for 24 hours. At the end the reaction was quenched by the addition of H$_2$O (10 mL) and evaporated under high vacuum to afford crude product, which was purified by C18 reverse phase to afford product III as a yellow solid (545 mg, 61%). $^1$H NMR (300 MHz, D$_2$O) δ 8.01 (s, 1H, H-5'), 4.52 (dd, J=8.3, 3.1 Hz, 1H, H-2"), 3.89 (dd, J=16.1, 9.3 Hz, 1H, H-2), 3.65 (dd, J=15.0, 2.8 Hz, 2H, H-1"), 3.59-3.43 (m, 2H, H-3), 2.85 (s, 9H, NMe$_3$), 2.79 (s, 3H, acetate); $^{13}$C NMR (101 MHz, D$_2$O) δ 171.7 (C-3"), 170.0 (C-1), 159.8 (C-2'), 156.6 (C-4'), 132.9 (C-5'), 64.3 (C-2), 56.7 (C-1"), 49.4 (NMe$_3$), 49.1 (C-2"), 34.7 (C-3); HRMS (ESI$^+$): m/z 349.1177 [M]$^+$. Calculated for C$_{12}$H$_{21}$N$_4$O$_6$S$^+$, found 349.1192 [M]$^+$ (FIG. 12).

3. Total Protein Extraction and Purification from *Mycobacterium smegmatis*

Mc$^2$155 (*M. smegmatis*) Growth Conditions

*M. smeg* culture (800 ml) was grown to exponential phase, and then dried to obtain 10 g of dry cells. The obtained pellets of *M. smeg* cells were thereafter stored at −80° C. until it was required.

Total Protein Extraction

*M. smeg* cells were sonicated for 35 minutes at 4° C. (25 pulsars), followed by the addition of potassium phosphate buffer (60 ml; pH 7). The solution was allowed to stir at 4° C. for 10 minutes and thereafter centrifuged at 3000 rpm for 20 min. The supernatant was collected, measured and then the appropriate amount of ammonium sulphate gradually added while stirring at 4° C. overnight to obtain 60-70% saturation.[28]

After precipitation of total protein the suspension was centrifuged at 4° C. at 3000 rpm for 20 min and stored at −20° C.

Total Protein Purification

The complex total protein ammonium salts precipitate was resuspended in buffer mixture (20 ml; pH 7) containing pyridoxal phosphate (10 ml; 20 μM), potassium phosphate buffer (8 ml; 50 mM; pH 7) and (2 ml; 1 mM EDTA).

Protein Calibration Curve

Figure 13:
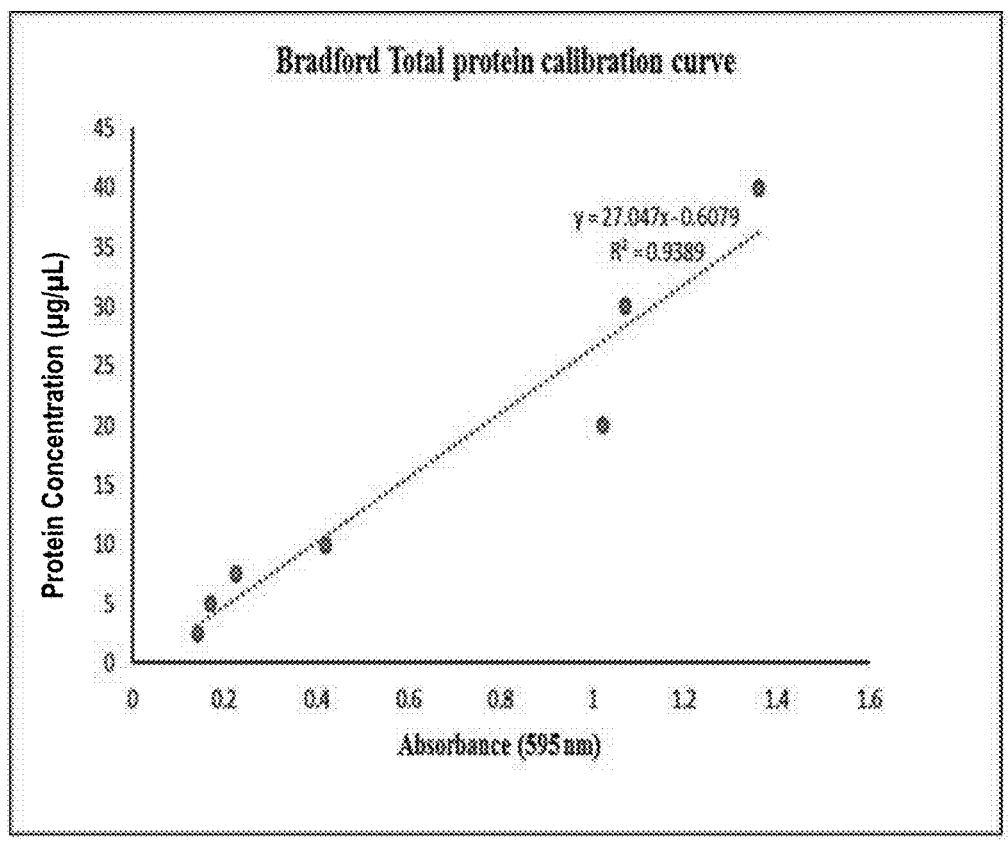
FIG. 13 Bradford protein concentration calibration curve.

In order to determine the total protein concentration, the protein Dc assay and the Bradford assays were used. The Bradford calibration curve was found to be more accurate than the protein Dc in the present case (FIG. 13).

The calculated *M. smeg* total protein concentration was found to be 10.33 μg/μl.

4. HPLC-ESI/MS (QTOF) Analysis

Materials and Methods

Analyses were carried out with a UHPLC Agilent 1290 Infinity Series (Germany), accurate mass spectrometer Agilent 6530 Quadrupole Time Of Flight (QTOF) equipped with an Agilent jet stream ionization source (positive ionization mode) (ESI$^+$) and column (Polaris 3 $C_{18}$ Ether 100×2 mm, particle size 3 μm, Agilent, Germany).

15 μL of concentrate samples were injected into the LCMS. Analyte separation was attempted in 0.1% formic acid in milli-Q water (solvent A) and mixture of 90% acetonitrile, 0.1% formic acid, 10% milli-Q water (solvent B) as mobile phase in an isochratic flow rate of 0.3 mL/min.

The system was controlled with the software packages Mass Hunter workstation software (Qualitative and Quantitative version B.05.00; Build 5.0.519.0, Agilent 2011, Germany).

Experimental LCMS

Figure 14A:
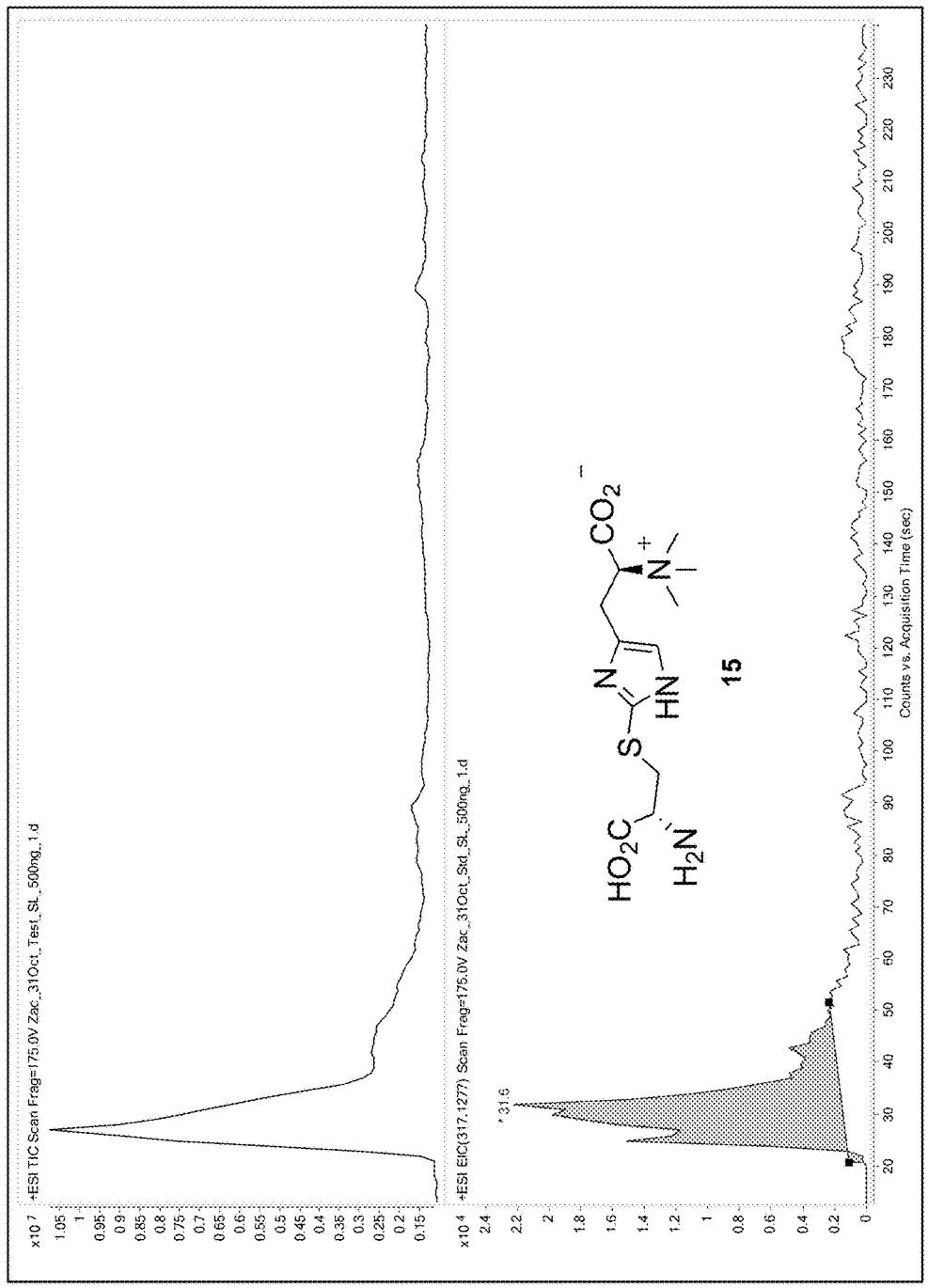
FIG. 14A TIC of S-(β-amino-β-carboxyethyl)ergothioneine sulfide (15).
Figure 14B:
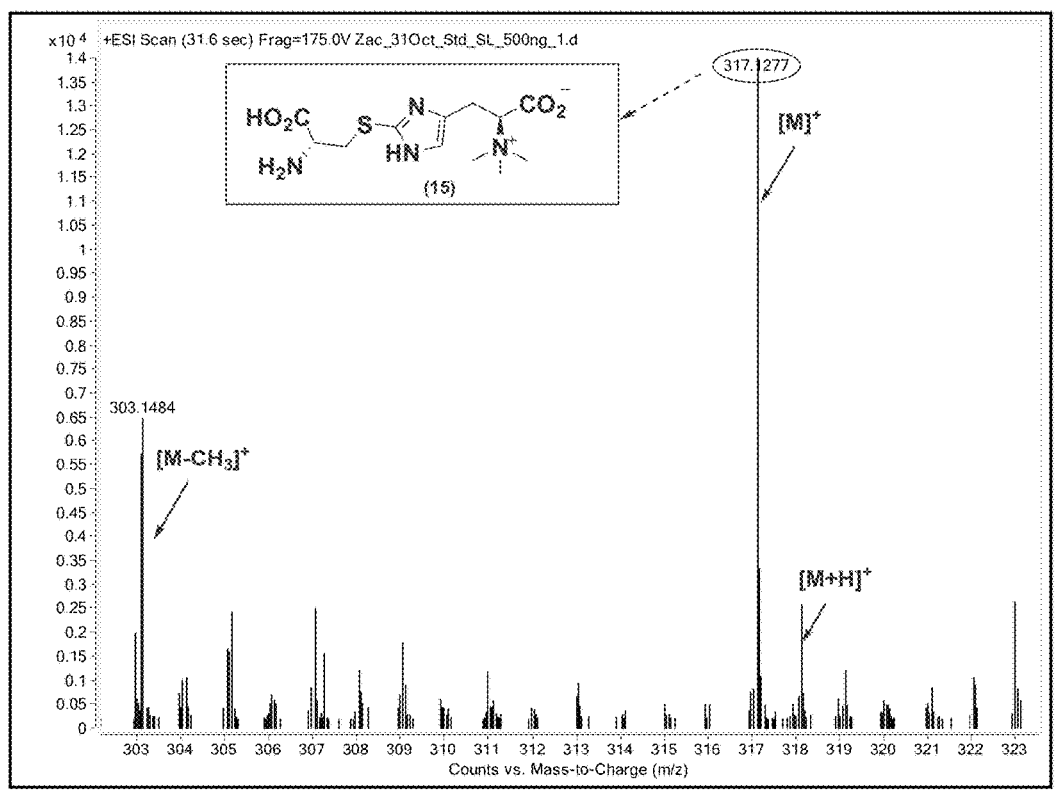
FIG. 14B ESI/QTOF mass spectra of S-(β-amino-β-carboxyethyl)ergothioneine sulfide (15) in positive ion mode.
Figure 15A:
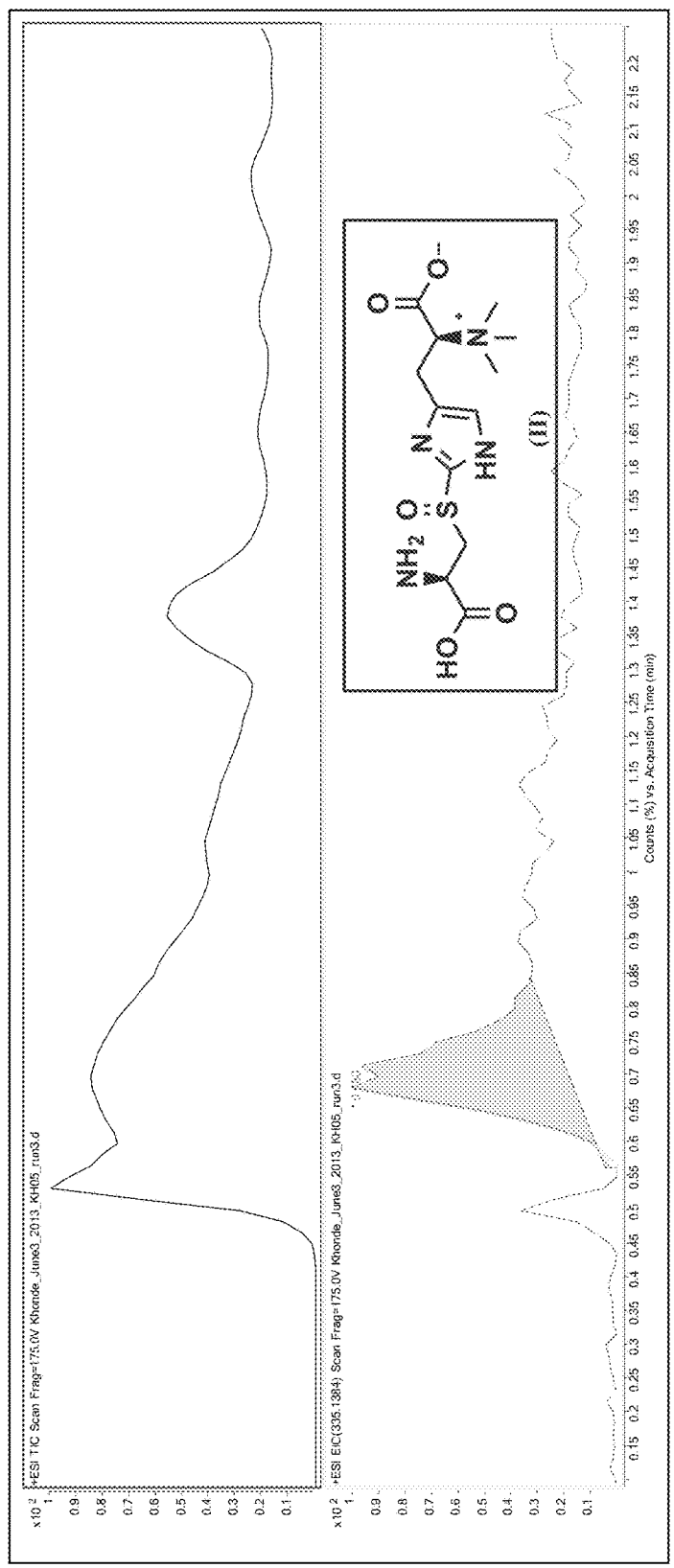
FIG. 15A TIC of S-(β-amino-β-carboxyethyl)ergothioneine sulfoxide (II).
Figure 15B:
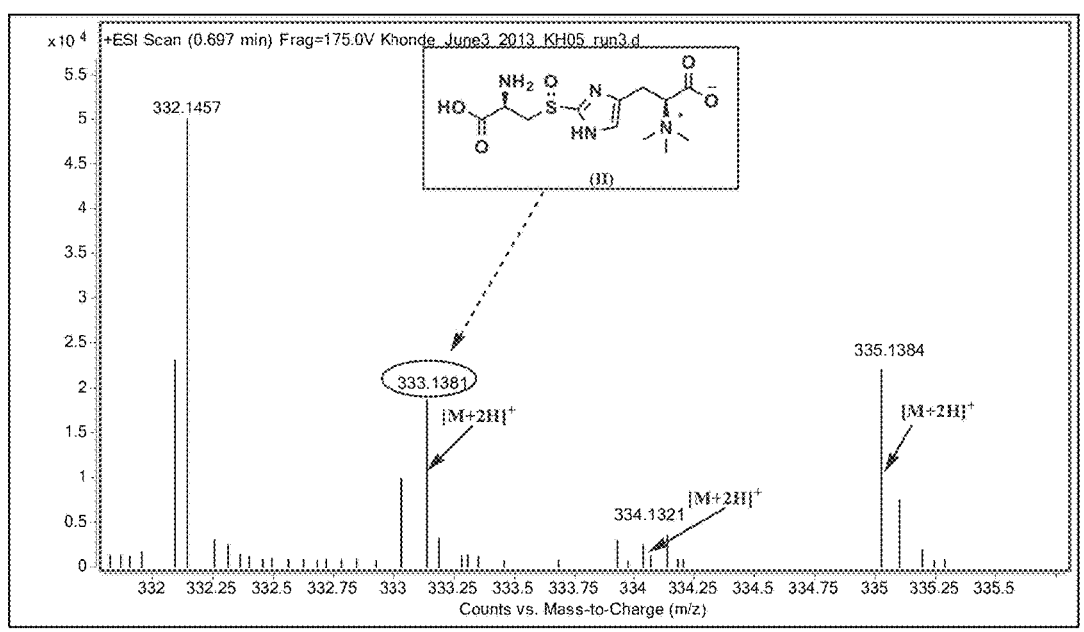
FIG. 15B ESI/QTOF mass spectra of S-(β-amino-β-carboxyethyl)ergothioneine sulfoxide (II) in positive ion mode.
Figure 16A:
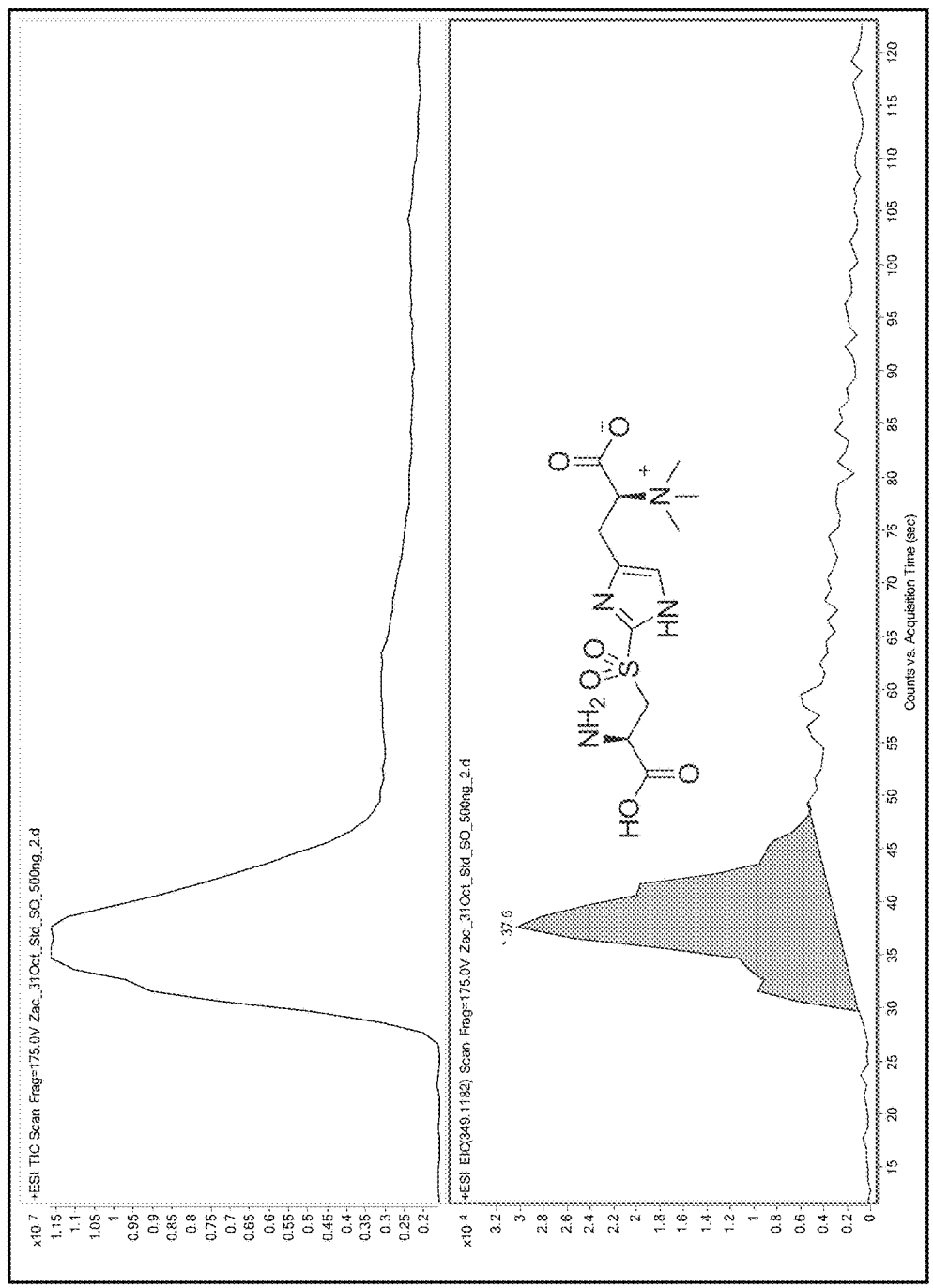
FIG. 16A TIC of S-(β-amino-β-carboxyethyl)ergothioneine sulfone (III).
Figure 16B:
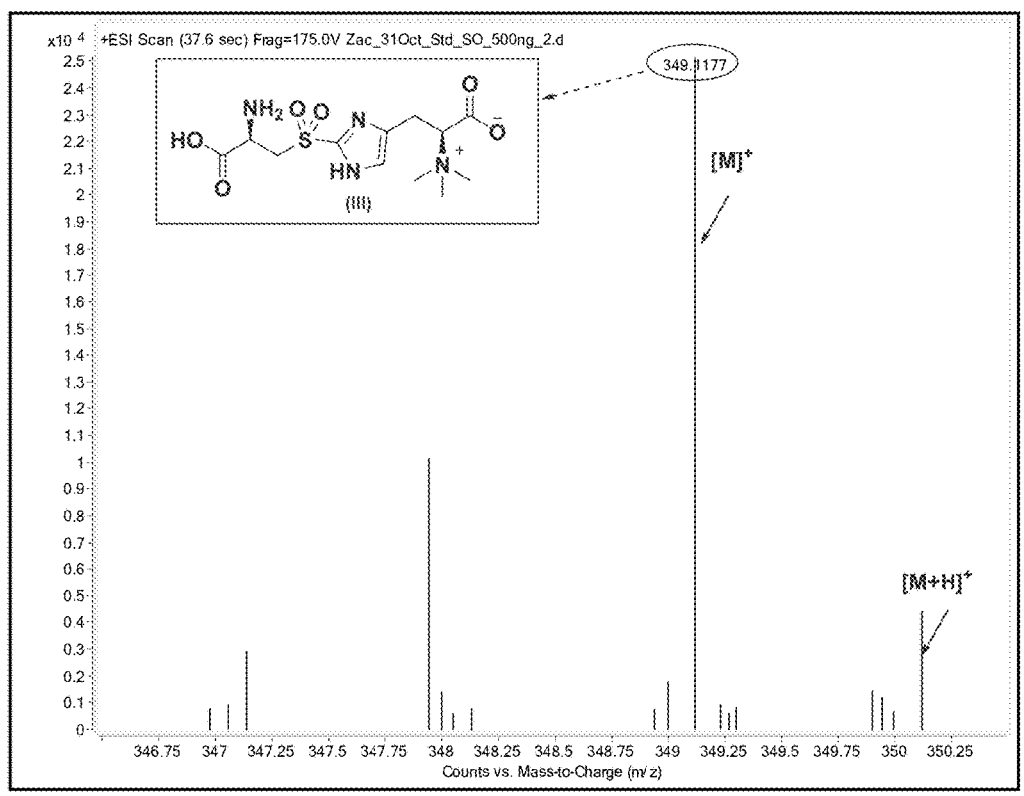
FIG. 16B ESI/QTOF mass spectra of S-(β-amino-β-carboxyethyl)ergothioneine sulfone (III) in positive ion mode.

Due to the polarity and charge on the quaternary ammonium group present in all metabolites, poor retention on the UHPLC (Eclipse+C18 RRHD 1.8 μm. 2.1×50) column was observed for ESH (RT=0.8 min). All later analysis were performed with an improved column as described in the section S3.1 (RT=1.5 min) (FIGS. 14 to 16).

In Vitro Reconstituted Biosynthesis of Ergothioneine in *Mycobacteria smegmatis*[12]

The experiments were performed in triplicate, repeated several times (more than three times) and these results were found to be reproducible.

ESH Calibration Curve

Figure 17:
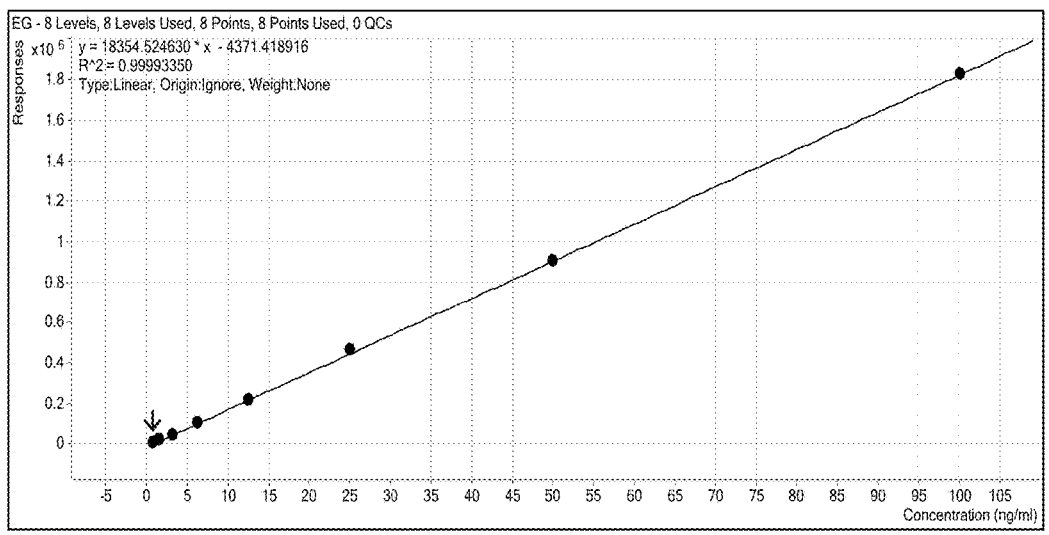
FIG. 17 Calibration curve of ESH.
Figure 18:
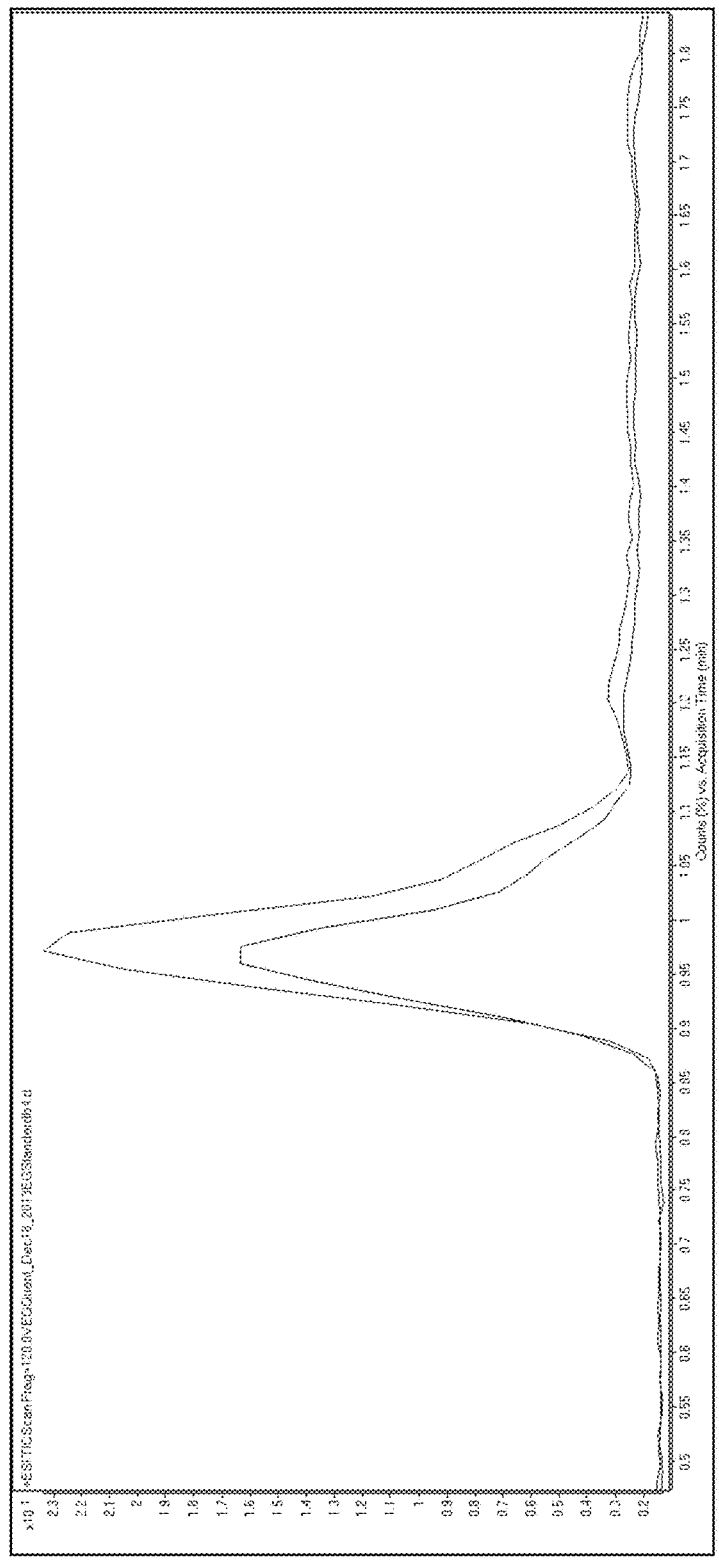
FIG. 18 Overlaid TIC of Ergothioneine. Retention time of 1.5 min.
Figure 19:
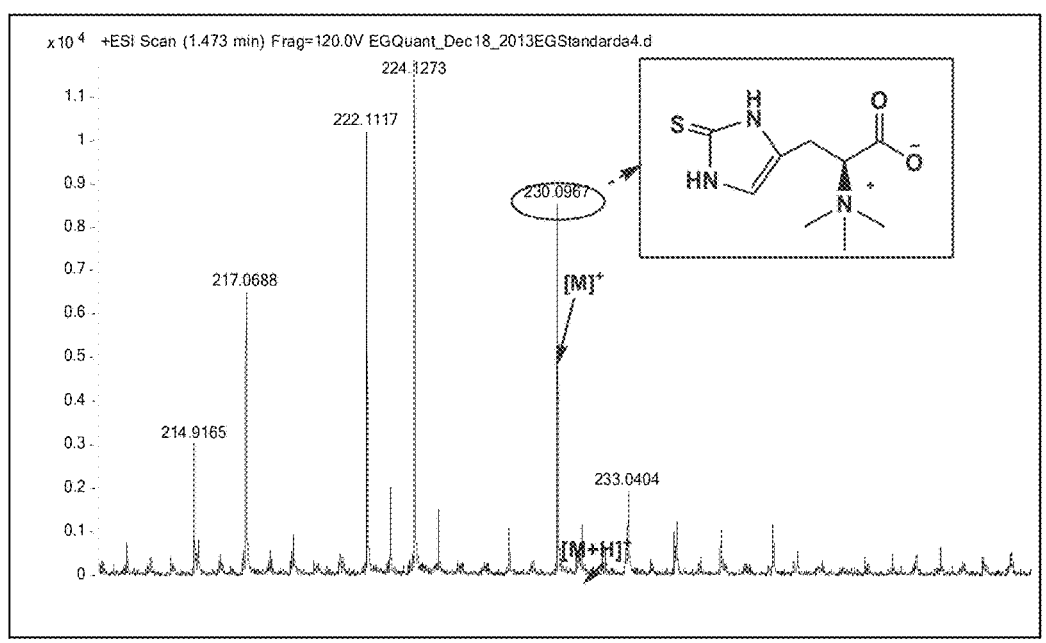
FIG. 19 ESI/QTOF mass spectra of ESH standard in positive ion mode.

In order to establish a calibration curve for the quantification of ESH, eight different concentrations (0.78, 1.56, 3.125, 6.25, 12.5, 25, 50, 100 ng/ml) of ESH were prepared in triplicate, giving a limit of quantification (LOQ) 0.78 ng/ml for ESH which was similar to the one found by L.-Z Wang et al.[15] The limit of detection (LOD) for ESH was 9 pg/mL. The retention time for ESH was 1.5 minute. Excellent symmetric peaks were achieved for both ESH standard and reactions samples analysed (FIGS. 17 to 19).

Figure 20:
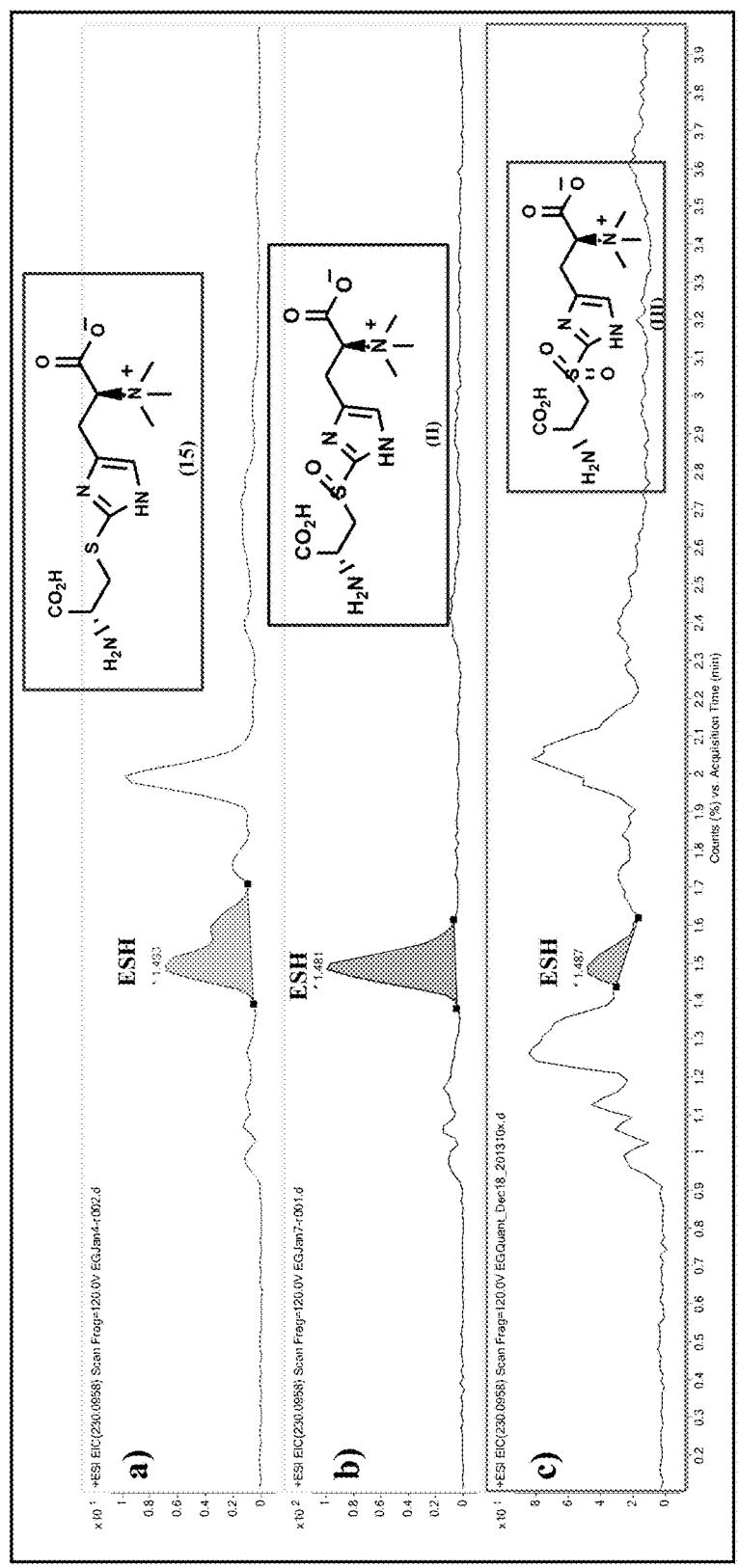
FIG. 20 TIC extracted for ESH in-vitro reconstititued experiment using substrate: (a) S-(β-amino-β-carboxyethyl) ergothioneine sulfide (15) as substrate, (b) S-(β-amino-β-carboxyethyl)ergothioneine sulfoxide (II) as substrate and (c) S-(β-amino-β-carboxyethyl)ergothioneine sulfone (III) as substrate.

Biotransformation of Substrates to Ergothioneine Using Crude *M. smegmatis* Enzymes Preparation Three sets of 100 μl reactions (1-4) containing 20 mM Tris HCl pH=7.4, 20 mM NaCl, 0.2 Mm $FeSO_4.7H_2O$, 0.5 mM mercaptoethanol, 83 μl of crude enzymes and 50 mM of either (1) S-(β-amino-β-carboxyethyl)ergothioneine sulfide (15) (2) S-(β-amino-β-carboxyethyl)ergothioneine sulfoxide (II) (3) S-(β-amino-β-carboxyethyl)ergothioneine sulfone (III) or (4) control (only crude enzymes no substrates). The crude enzyme reactions were incubated for 1 day at 37° C. The reaction was stopped by heating the mixture at 90° C. for 2 min followed by lyophilisation and subsequent reconstitution in LC buffer before analysis by LC/MS (FIG. 20).

Non Enzymatic Cleavage of C—S Bond Catalysed by PLP

Three sets of 100 μl reactions (1-3) containing 20 mM Tris HCl pH=7.4, and 50 mM of either (1) S-(β-amino-β-carboxyethyl)ergothioneine sulfide (15) and PLP (2) S-(β-amino-β-carboxyethyl)ergothioneine sulfoxide (II) and PLP or (3) S-(β-amino-βcarboxyethyl)ergothioneine sulfone (III) and PLP. The non-enzymatic reactions were incubated for 1 day at 37° C., followed by lyophilisation and subsequent reconstitution in LC buffer before analysis by LC/MS (FIGS. 2 and 3).

5. Isotopic Labelling

Hercynine-$d_3$ (7) was synthesized in a two-step reaction starting with commercially available L-histidine (Scheme 2). The first step involved reductive amination using aqueous formaldehyde and sodium triacetoxyborohydride to give N,N-dimethyl histidine (6). The second step involved the quaternarization of the crude N,N-dimethyl histidine (6) using methyl-$d_3$ iodide under basic conditions to give the hercynine-$d_3$ (7).

ESH-$d_3$ (10) was synthesized in two sequential reaction steps starting with the S-tert-butyl protected 2-mercapto-histidine (9), derived from mercapto histidine (8).[21] Selective N-methylation with methyl-$d_3$ iodide, followed by S-tert-butyl deprotection using 2-mercaptopropionic acid (tert-butyl scavenger) in HCl gave ESH-$d_3$ (10).

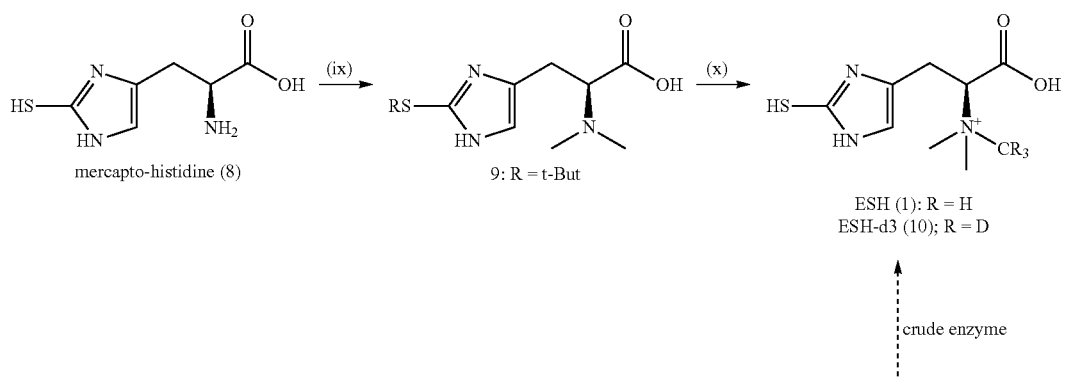

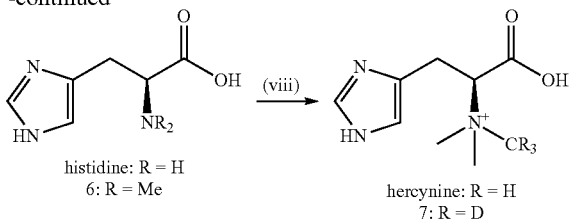

histidine: R = H
6: R = Me hercynine: R = H
7: R = D

Synthesis of Hercynine and Ergothioneine Deuterated Compounds

REFERENCES

1. Robert, C. F. *Biochimica et Biophysica Acta,* 2013, 1830, 3182-3198.
2. Van Laer, K.; Hamilton, C. J.; Messens, J. *Antioxidants and Redox Signaling.* 2013, 18, 1642-1653.
3. Ta, P.; Buchmeier, N.; Newton, G. L.; Rawat, M.; Fahey, R. C. *J. Bacteriol.,* 2011, 8, 1981-1990.
4. Emani, C. S.; Williams, M. J.; Wiid, I. J.; Hiten, N. F; Viljoen, A. J.; Pietersen, R-D.; Van Helden, P. D.; Baker, B. *Antimicrob. Agents Chemother.* 2013, 57, 3202-3207.
5. Ariyanayagam, M. R.; Fairlamb A. H. *Molecular and Biochemical Parasitology,* 2001, 115, 189-198.
6. Grundemann D.; Harlfinger S.; Golz S.; Geerts A.; Lazar A.; Berkels R.; Jung N.; Rubbert A.; Schomig E. *PNAS,* 2005, 102, 5256-5261.
7. Cheah I. K.; Halliwell B. *Biochim Biophys Acta.* 2012, 1822, 784-793.
8. Heath H.; Wildy, J., *Biochem. J.,* 1957, 65, 220-222.
9. Melville, D. B.; Eich, S.; Ludwig, M. L. *J. Biol. Chem.,* 1957, 224, 871-877.
10. Genghof, D. S.; Van Damme, O. *J. Bacteriol.,* 1962, 95, 340-344.
11. Ishikawa, Y.; Israel S. E.; Melville D. B. *J. Biol. Chem.,* 1974, 249, 4420-4427.
12. Seebeck F. P. *J. Am. Chem. Soc.* 2010, 132, 6632-6633. Also Blast sequence alignment analysis of *M. Smeg* EgtE against the β-lyases of *T. denticola* and *E. tasmaniensis* (not shown).
13. Mashabela G. T. M.; Seebeck F. P. *Chem. Commun.,* 2013, 49, 7714-7716.
14. Song H.; Leninger M; Lee N; Liu P. *Organic Letters,* 2013, 15, 4854-4857.
15. Ishikawa, Y.; Israel S. E.; Melville D. B. *J. Biol. Chem.,* 1974, 249, 4420-4427.
16. Schwimmer S.; Ryan C. A.; Wong F. *J. Biol. Chem.,* 1964, 239, 777-782.
17. Bryan, J. J.; Hinks, R. S.; Hultin, P. G. *Can. J. Chem.,* 1985, 63, 452-456.
18. Wild, H., *J. Org. Chem.,* 1994, 59, 2748-2761.
19. Sato, K.; Omote, M.; Ando, A.; Kumadaki, I. *Org. Lett.,* 2004, 6, 4359-4361.
20. Erdelmeier, I.; Daunay, S.; Lebel, R; Farescour, L.; Yadan J-C. *Green Chem.,* 2012, 14, 2256-2265.
21. Trampota, M.; United States Patent, 2010, U.S. Pat. No. 7,767,826, B2.
22. Toth, K.; Richard, J. P. *J. Am. Chem. Soc.,* 2007, 129, 3013-3021.
23. Krupka, H. I.; Huber R.; Holt S. C.; Clausen T. *EMBO J.* 2000, 19, 3168-3178.
24. Flavin, M; Segal A. *J. Biol. Chem.,* 1964, 239, 2220-2227.
25. Sivaramakrishnan, S.; Cummings, A. H.; Gates, K. S. *Bioorganic & Medicinal Chemistry Letters,* 2010, 20, 444-447.
26. Rostami, A.; Hassanian, F.; Choghamarani, A. G. and Saadati, S., *Phosporus, sulfur and silicon,* 2013, 188, 833-838
27. Rostami, A. and Akradi, J., *Tetrahedron lett.,* 2010, 51, 3501-3503
28. Ashraf, S. A., *J. Microbiol.,* 2011, 130-140

The invention claimed is:

1. A process for synthesising a compound of formula V

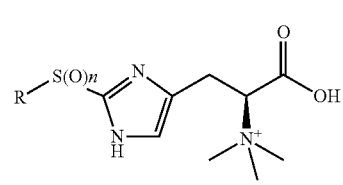

wherein:

n is 0, 1 or 2; and

R is H or

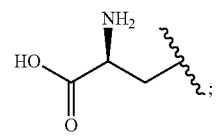

or a physiologically acceptable salt, tautomer, stereoisomer or mixture of stereoisomers thereof, the process comprising the steps of:

a) deprotecting a N-benzyl protected histidine of formula 11 to form N-benzyl histidine of formula 12

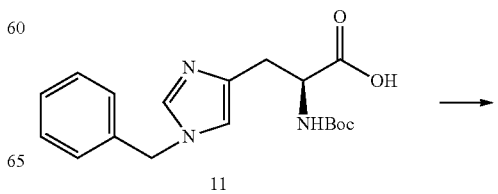

11

-continued

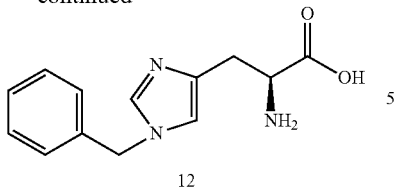
12 b) converting compound 12 to (S)-3-(1-benzyl-1H-imidazol-4-yl)-2-(dimethylamino)propanoic acid of formula 13

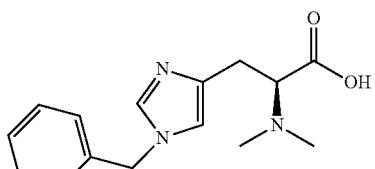
13 c) converting compound 13 to (2S)-N,N,N-2-trimethylethanaminium-3-(1-benzyl-1H-imidazol-4-yl)propanoic acid of formula 14

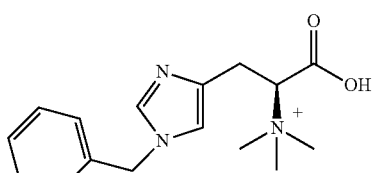
14 d) brominating the imidazole ring of the compound of formula 14 to form 5-bromohercynine lactone; and

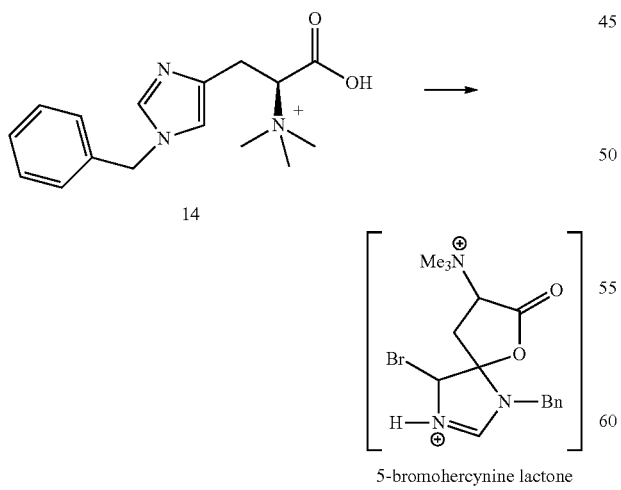
5-bromohercynine lactone e) converting the 5-bromohercynine lactone of step (d) to (β-amino-β-carboxyethyl)ergothioneine sulfide of formula 15

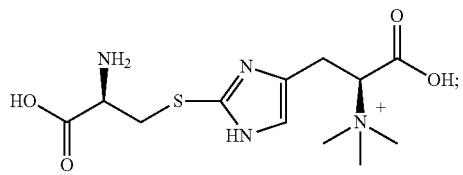
15 wherein the process optionally further includes any one of steps (f) to (h):

f) converting the compound of formula 15 to a sulfoxide of formula II

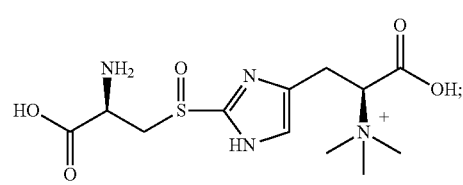
II or g) converting the compound of formula 15 to a sulfone of formula III

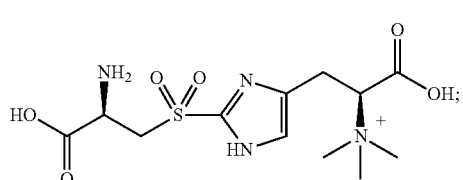
III or h) converting the compound of formula 15 to ergothioneine (ESH) of formula IV

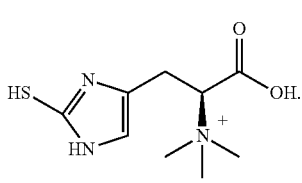
IV

2. The process according to claim 1, wherein
n is 0; and
R is

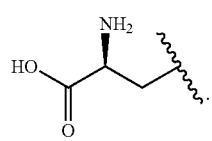 [SMILES: *C[C@H](N)C(=O)O]

3. The process according to claim 1, wherein
n is 1; and
R is

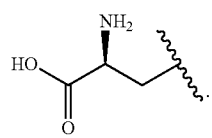

4. The process according to claim 1, wherein
n is 2; and
R is

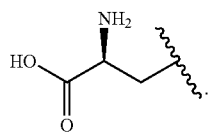

5. The process according to claim 1, wherein
n is 0; and
R is H.

6. The process according to claim 1, wherein the compound of formula V is selected from the group consisting of:

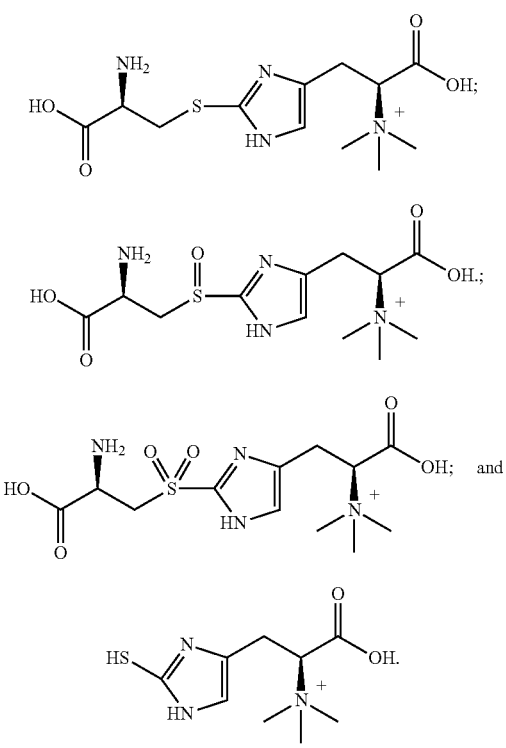

7. The process according to claim 1, wherein the compound of formula 11 is a N$^\alpha$-Boc-N(im)-benzyl protected L-histidine.

8. The process according to claim 1, wherein dimethylformamide (DMF) and N-bromosuccinimide (NBS) are used in step (d) to form the 5-bromohercynine lactone.

9. The process according to claim 8, wherein at least 2 mol equivalents of NBS relative to compound 14 are used in step (d).

10. The process according to claim 1, wherein the 5-bromohercynine lactone is a reactive intermediate formed during step (d) prior to performing step (e).

11. The process according to claim 1, wherein cysteine is used in step (e) to form the compound of formula 15.

12. The process according to claim 1, wherein thioacetic acid is used in step (e) to form the compound of formula 15.

13. The process according to claim 1, wherein steps (d) and (e) are performed in one pot synthesis.

14. The process according to claim 1, wherein pyridoxal-5 phosphate (PLP) is used in step (h) to form the ergothioneine of formula IV.

15. The process according to claim 1, wherein the sulfoxide of formula II formed in step (f) is further converted to ergothioneine of formula IV.

16. The process according to claim 15, wherein the sulfoxide of formula II is contacted with an enzyme encoded by the egtE gene to form the ergothioneine of formula IV.

17. The process according to claim 15, wherein the sulfoxide of formula II is contacted with EgtE enzyme to form the ergothioneine of formula IV.

18. The process according to claim 1, wherein the sulfide of formula 15 formed in step (e), or any one of the intermediate compounds formed in the process, is labelled with a stable isotope.

19. The process according to claim 18, wherein the isotope is deuterium.

20. The process according to claim 18, wherein the labelled intermediate compound is 5-bromohercynine.

* * * * *